US012629355B2

(12) United States Patent
Ullah et al.

(10) Patent No.: US 12,629,355 B2
(45) Date of Patent: May 19, 2026

(54) DRUG INHIBITOR AGAINST MIGRATION AND INVASION OF CANCER CELLS AND METHODS OF TREATING AGAINST METASTASIS OF CANCER CELLS

(71) Applicants: HOWARD UNIVERSITY, Washington, DC (US); GEORGETOWN UNIVERSITY, Washington, DC (US)

(72) Inventors: Hemayet Ullah, Washington, DC (US); Sivanesan Dakshanamurthy, Herndon, VA (US)

(73) Assignees: Howard University, Washington, DC (US); GEORGETOWN UNIVERSITY, Washington, DC (US)

( * ) Notice: Subject to any disclaimer, the term of this patent is extended or adjusted under 35 U.S.C. 154(b) by 202 days.

(21) Appl. No.: 17/598,543

(22) PCT Filed: Mar. 25, 2020

(86) PCT No.: PCT/US2020/024610
§ 371 (c)(1),
(2) Date: Sep. 27, 2021

(87) PCT Pub. No.: WO2020/198301
PCT Pub. Date: Oct. 1, 2020

(65) Prior Publication Data
US 2022/0168277 A1 Jun. 2, 2022

Related U.S. Application Data

(60) Provisional application No. 62/823,278, filed on Mar. 25, 2019.

(51) Int. Cl.
*A61K 31/4196* (2006.01)
*A61P 35/00* (2006.01)
*A61P 35/04* (2006.01)

(52) U.S. Cl.
CPC .......... *A61K 31/4196* (2013.01); *A61P 35/00* (2018.01)

(58) Field of Classification Search
CPC ....... A61K 31/4196; A61P 35/00; A61P 35/04
See application file for complete search history.

(56) References Cited

U.S. PATENT DOCUMENTS

| | | | | |
|---|---|---|---|---|
| 5,658,720 A | * | 8/1997 | Ikesu | G03C 7/3835 430/558 |
| 11,596,623 B2 | * | 3/2023 | Ullah | A61K 31/4196 |
| 2008/0045514 A1 | | 2/2008 | Cai et al. | |

FOREIGN PATENT DOCUMENTS

| | | | | |
|---|---|---|---|---|
| WO | 2006/103345 A1 | 10/2006 | | |
| WO | WO-2008157407 A2 | * 12/2008 | .......... | C07D 249/12 |

OTHER PUBLICATIONS

Valastyan S, Weinberg RA. Tumor metastasis: molecular insights and evolving paradigms. Cell. Oct. 14, 2011;147(2):275-92. doi: 10.1016/j.cell.2011.09.024. PMID: 22000009; PMCID: PMC3261217. (Year: 2011).*
Cecil Textbook of Medicine, 20th Ed, vol. 1, 1997 (Year: 1997) (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022) (Year: 2022).*
Zhang D, Wang Q, Zhu T, Cao J, Zhang X, Wang J, Wang X, Li Y, Shen B, Zhang J. RACK1 promotes the proliferation of THP1 acute myeloid leukemia cells. Mol Cell Biochem. Dec. 2013;384(1-2):197-202. doi: 10.1007/s11010-013-1798-0. Epub Sep. 3, 2013. PMID: 24000012. (Year: 2013).*
Campagne et al., "RACK1, a clue to the diagnosis of cutaneous melanomas in horses", BMC Veterinary Research, 2012, pp. 1-9, vol. 8, 95.
Pablo Lopez-Bergami et al., "Receptor for RACK1 Mediates Activation of JNK by Protein Kinase C", Molecular Cell, Aug. 5, 2005, pp. 309-320, vol. 19, No. 3.
"4-Amino-5-(3,5-dichlorophenyl)-4H-1,2,4-triazole-3-thiol", PubChem, Jul. 19, 2005, pp. 1-10, [online], [retrieved on May 6, 2020]. Retrieved from the Internet <URL:https://pubchem.ncbi.nlm.nih.gov/compound/2794850>; p. 2.
Hemayet Ullah et al., "Host targeted antiviral (HTA): functional inhibitor compounds of scaffold protein RACK1 inhibit herpes simplex virus proliferation", Oncotarget, May 14, 2019, pp. 3209-3226, vol. 10, No. 35.
Written Opinion for PCT/US2020/024610, dated Jun. 9, 2020.
International Search Report for PCT/US2020/024610, dated Jun. 9, 2020.

* cited by examiner

*Primary Examiner* — Bruck Kifle
*Assistant Examiner* — Kevin S Martin
(74) *Attorney, Agent, or Firm* — Sughrue Mion, PLLC

(57) ABSTRACT

A method for treating against, or at least inhibiting or suppressing, the proliferation of a cancer involves administering a compound, a tautomer, or a pharmaceutically acceptable salt thereof, in an amount effective for inhibiting metastasis of cancer cells, wherein the compound is represented by the formula (1):

wherein each $R_1$ independent of the other and represents a halogen atom selected from the group consisting of bromo, chloro, fluoro and iodo.

8 Claims, 24 Drawing Sheets

Specification includes a Sequence Listing.

SD29-14 blocks filipodia development needed for migration in the U251 cells (Glioblastoma- Brain Cancer)

DMSO + TGF (5 ng/ml)
On Matrigel no membrane 48h drug treatment. 18 hours on Matrigel (no serum +/- TGF)

SD29-14 (100 uM) + TGF (5ng/ml)

SD29-14 blocks Filipodia development in MCF-7 cells

SD29-14 (100 uM) + TGF (5ng/ml)

DMSO + TGF (5 ng/ml)
On Matrigel no membrane 48h drug treatment. 18 hours on Matrigel (no serum +/- TGF)

Low concentration of SD29-14 is also effective in blocking migration structures in 72h grown U251 cells Low concentration of SD29-14 is also effective in blocking migration structures in 72h grown MCF-7 cells SD29-14 (100 uM)

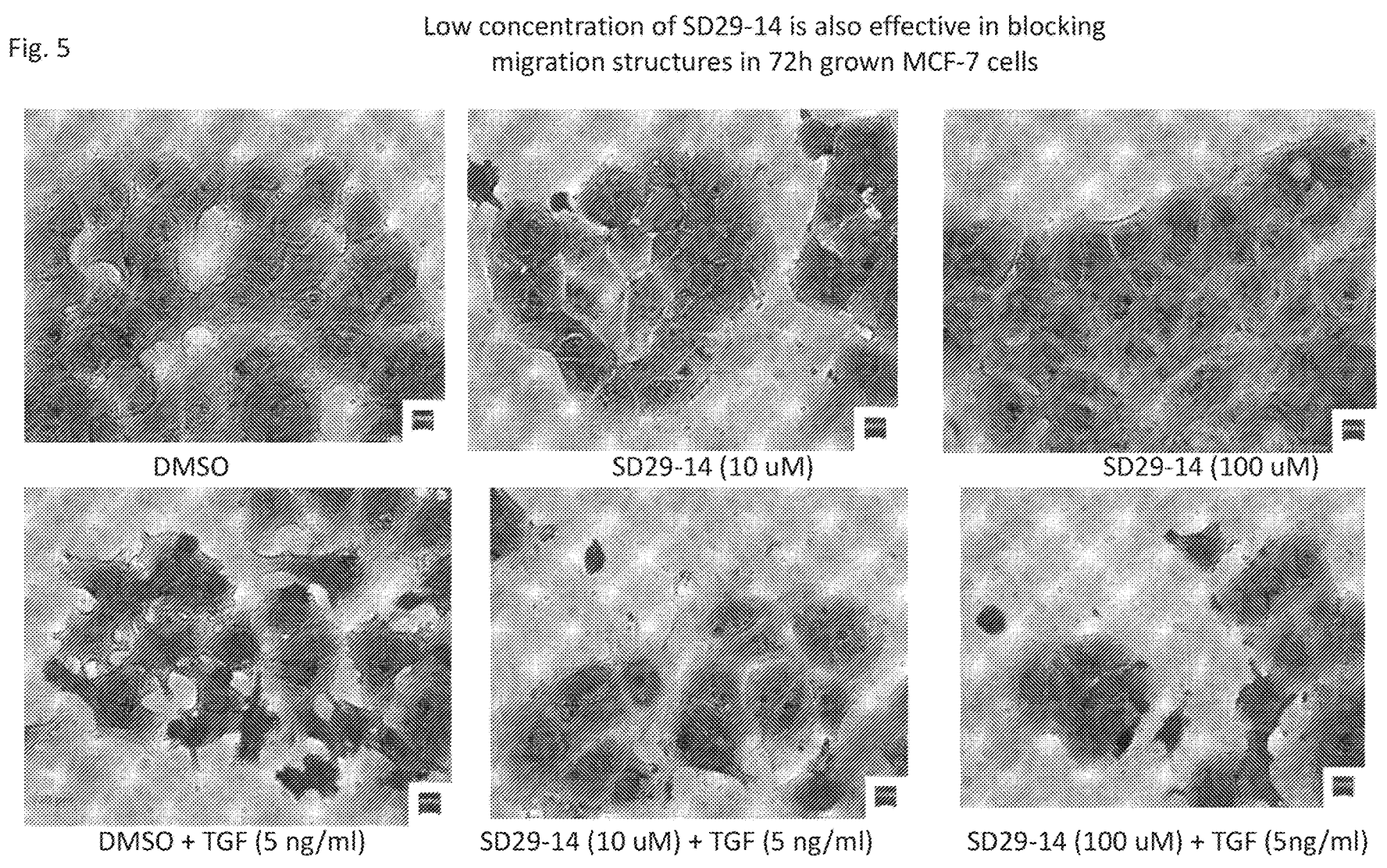

SD29-14 (100 uM) + TGF (5 ng/ml)

SD29-14 (10 uM)

SD29-14 (10 uM) + TGF (5 ng/ml)

DMSO

DMSO + TGF (5 ng/ml)

Fig. 5

Fig. 6          SD29-14 blocks Stress Fiber development in the lamellipodia of U251 cells

RACK1

Ponceau

6d MCF-7 2X drugs (every 3 days)
1= D+C   2= 14-100 + C   3= 12-100+C   4= D+ TGF-beta (4 ug/ml)
5 = 14-100 + TGF   6= 12-100 + TGF   7= 14-10 + TGF
Ponceau on TGX gel in Novex II gel rig
RACK1 Western on XT-MES gel (18 well)

Glioblastoma U251-MG cells show inhibition of EMT by SD29-14
6 days old (24h starve), replenish drugs and TGF-b1 after 3 days SD29-14 blocks the migration of U251 cells

Fig. 9

SD29-14 blocks migration through transwell membrane (8 um pore size)

DMSO + TGF (2 ng/ml)

SD29-14 (100 uM) + TGF (2ng/ml)

Transwell: Upper chamber serum free with DMSO or SD29-14; lower chamber with serum media
No Matrigel Fig. 11
SD29-14 inhibits Lamellipodia/Filipodia co-localization of RACK1 with ECM protein LamB1 in U251 cells
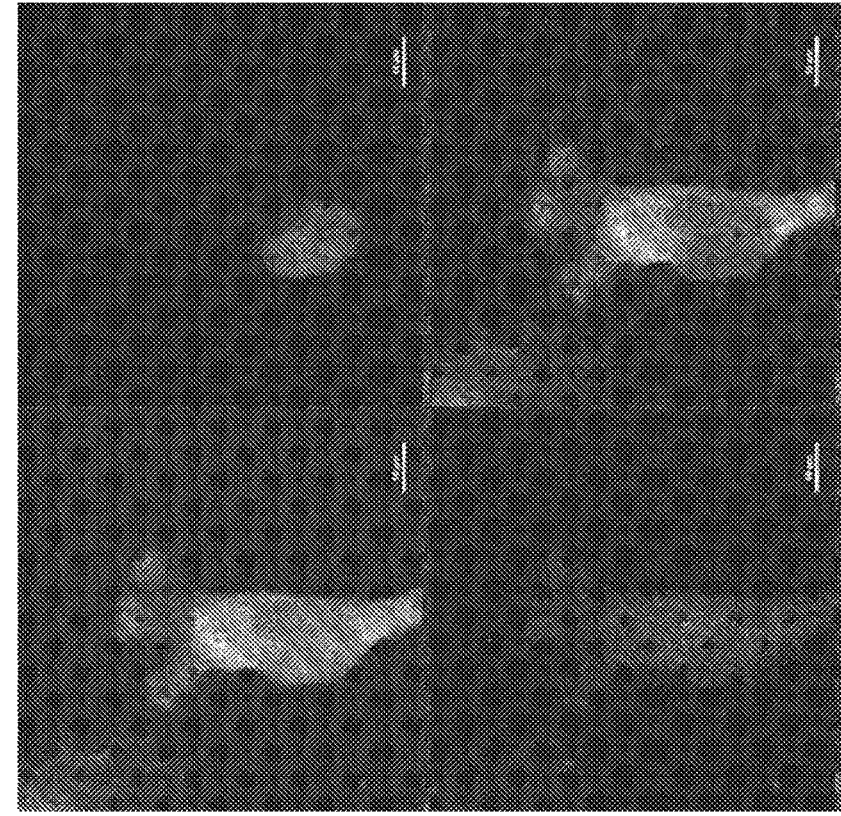
SD29-14 (100 uM) + TGF (5ng/ml)
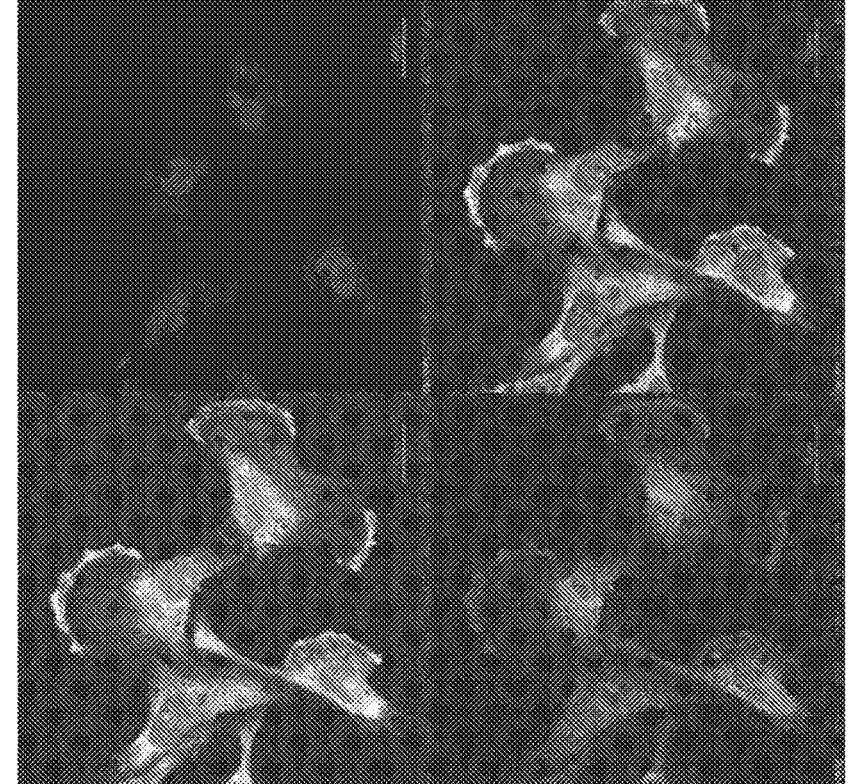
DMSO + TGF (5 ng/ml) 72h RACK1 and FAK Colocalizes in the tip of developing Filipodia/Lamellipodia in U251 cells SD29-14 inhibits colocalization of non-phosphor FAK and RACK1 in the leading edges of Lamellipodia in U251 cells 24h pre-treat and 24h treat with drugs + C (no TGF treatment)

DMSO + C

SD29-14 (100 uM) + C

FAK antibody from Genetex (Red); RACK1 coupled with FITC (green) from SCBT

RACK1 Y248 phosphorylation inhibitor compound blocks Tyrosine397 phosphorylation of FAK in MCF-7 cancer cells
- a key event for Invasion and migration Green anti-pFAK (tyrosine397); red anti-RACK1

SD29-14 +TGF-beta (5 ng/ml)

DMSO +TGF-beta (5 ng/ml)

1/3/19 5 days 1X drugs

Fig. 15 RACK1 Y248 phosphorylation inhibitor compound blocks Tyrosine397 phosphorylation of FAK in U251 cancer cell- a key event for Invasion and migration
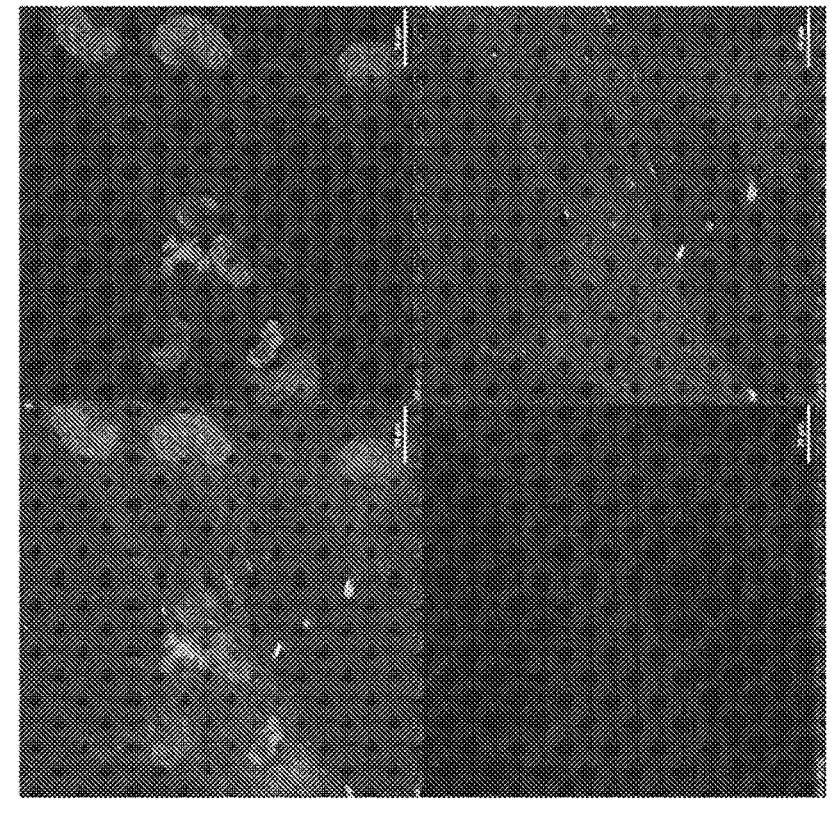
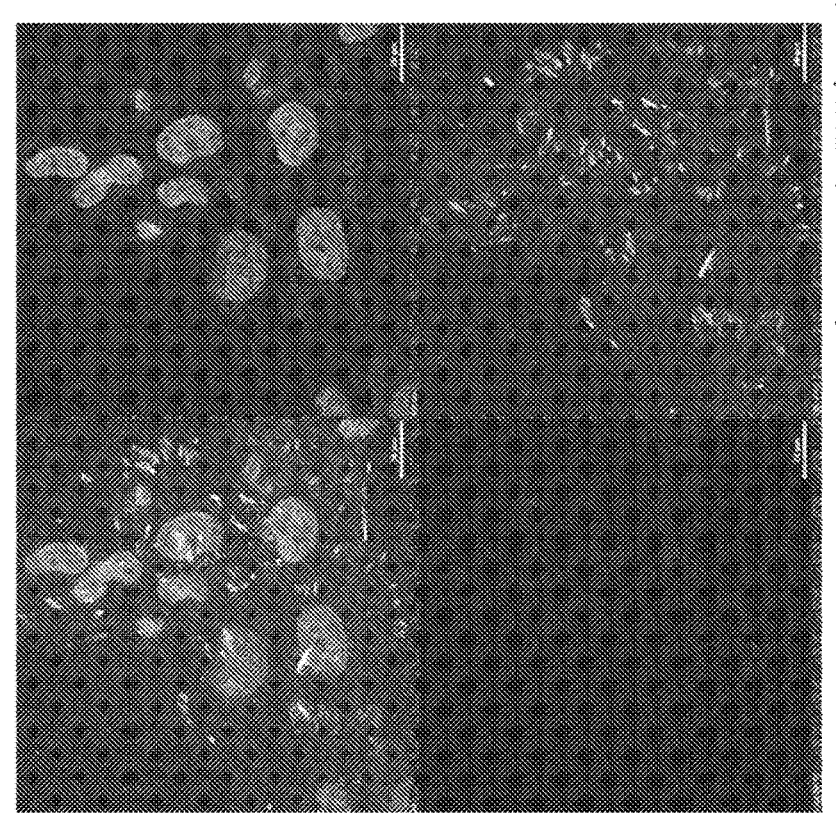
DMSO +TGF-beta (5 ng/ml)
SD29-14 +TGF-beta (5 ng/ml)
Green anti-pFAK (tyrosine397); red anti-RACK1
1/3/19 5 days 1X drugs U251 Cells 20h on Matrigel covered coverslip with DMSO U251 cells 20h on Matrigel covered coverslip with SD29-14 (10 uM)

U251 cells 20h on Matrigel covered coverslip with SD29-14 (100 uM)

100 µm

U251 10^5 cells 20h on Matrigel covered coverslip

SD29-14 (100 uM)

SD29-14 (10 uM)

DMSO

Localized F-Actin Foci helps develop stress fiber based directional filopodia development while SD29-14 prevents organized Filopodia development
Fig. 20
SD29-14 (10 uM) + 2 ng/ml TGF-b1
DMSO + 2 ng/ml TGF-b1
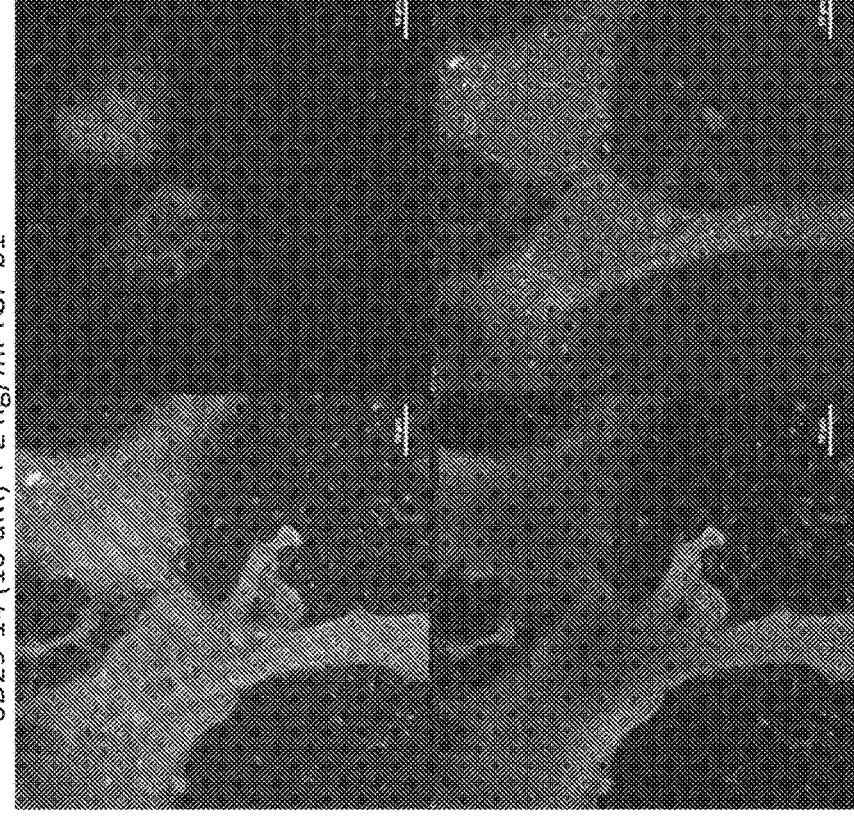
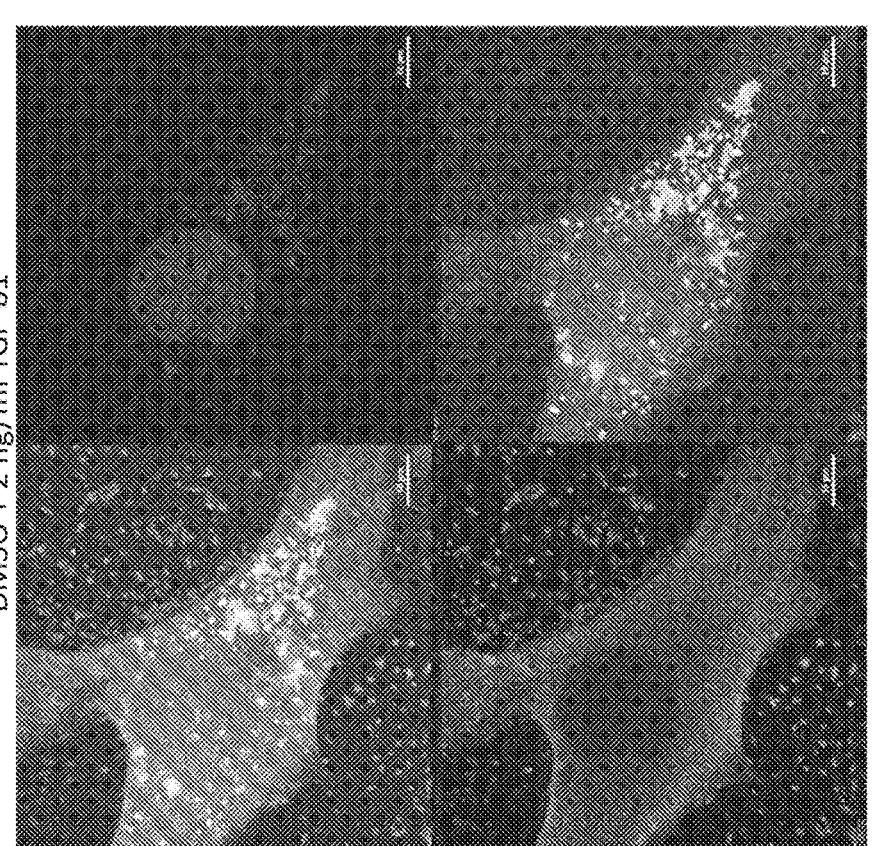
U251 96h on coverslip (no Matrigel) : F-Actin FITC (Phalloidin Green) ; pFAK 397 TRITC (Red) 1-21-19

Fig. 21
Inhibition of Vimentin (EMT marker) can prevent cancer cell invasive structures
DMSO SD29-14 (100 uM)
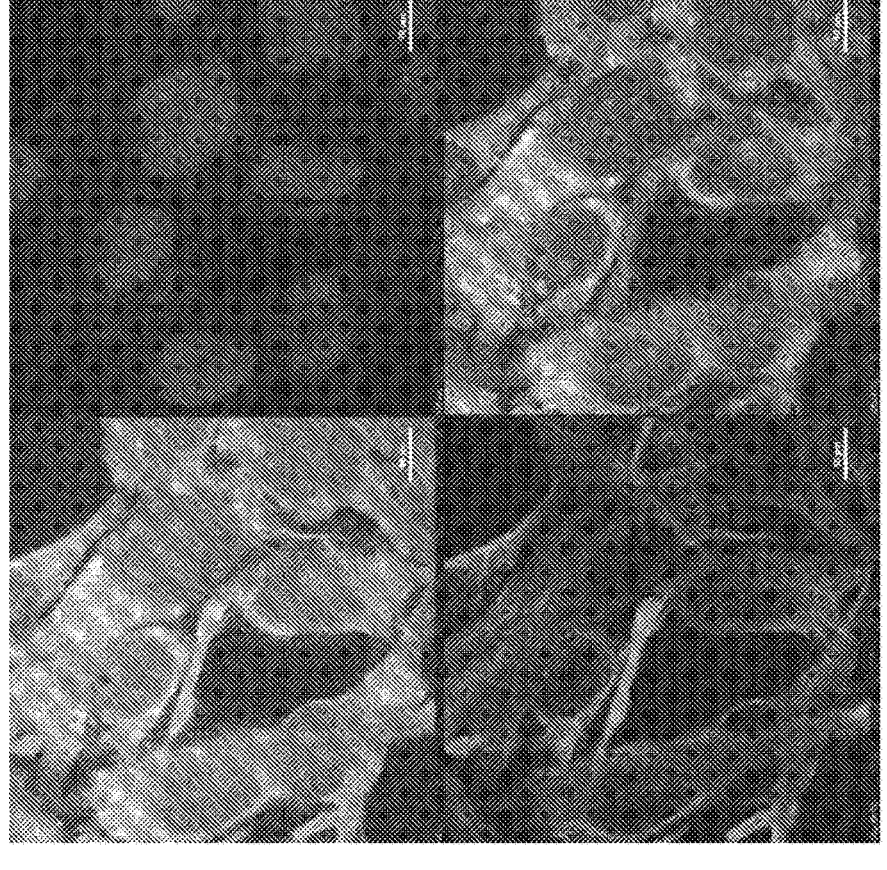
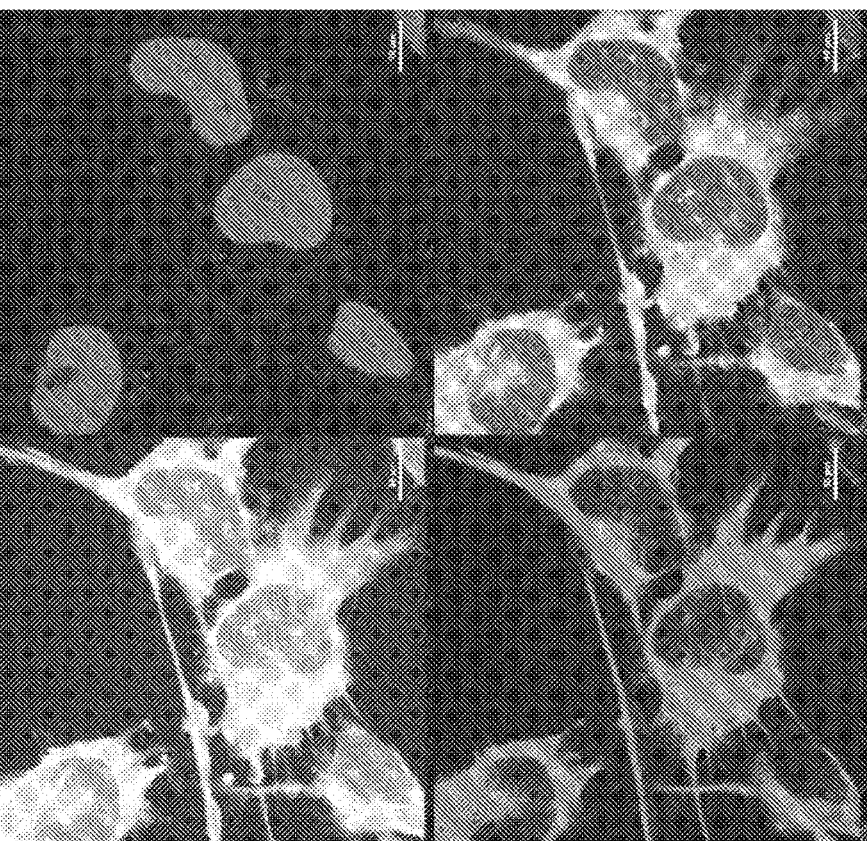
U251 20h on coverslip with Matrigel : Vimentin (TRITC-Red) and RACK1 (FITC-Green)

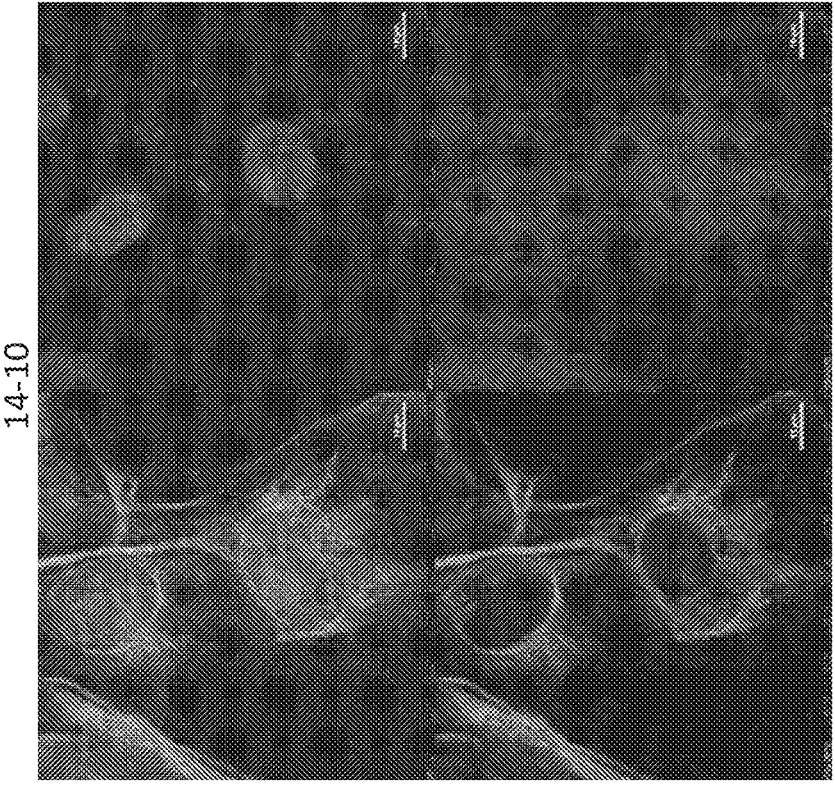
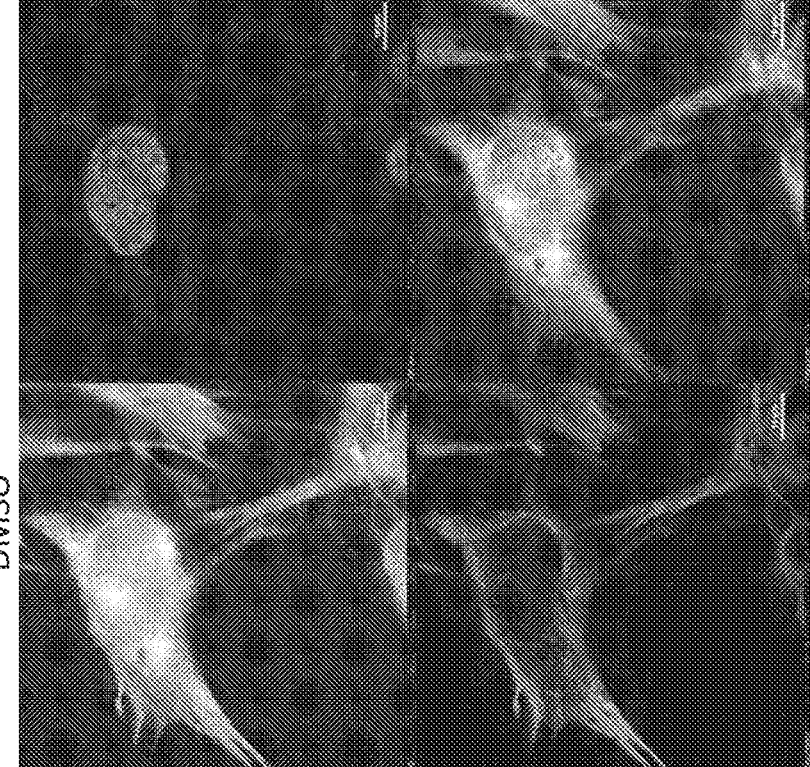
20h on coverslip with matrigel
Vimentin (TRITC) Actin- Phalloidin (FITC)
Fig. 22

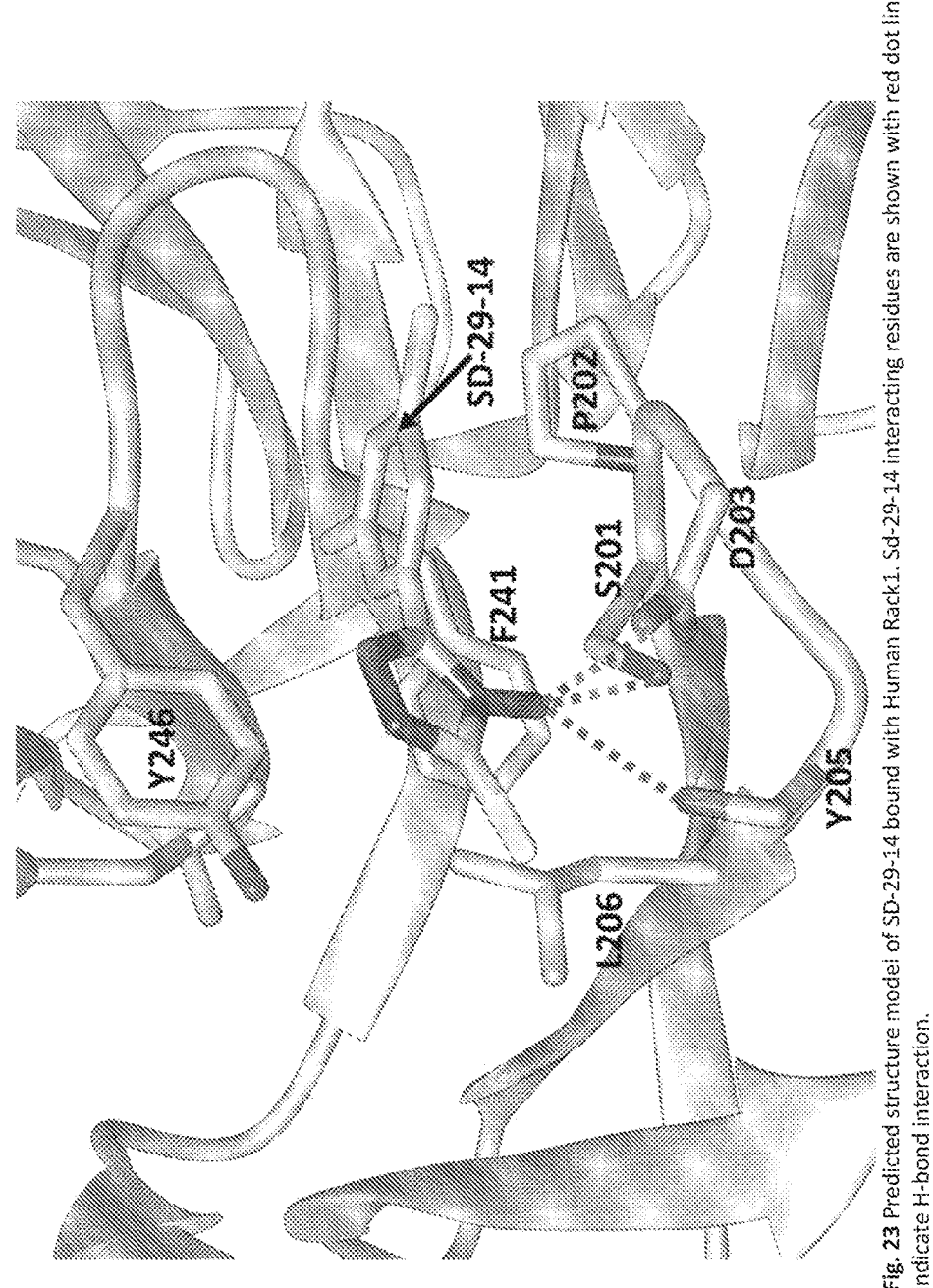
Fig. 23 Predicted structure model of SD-29-14 bound with Human Rack1. Sd-29-14 interacting residues are shown with red dot line indicate H-bond interaction.

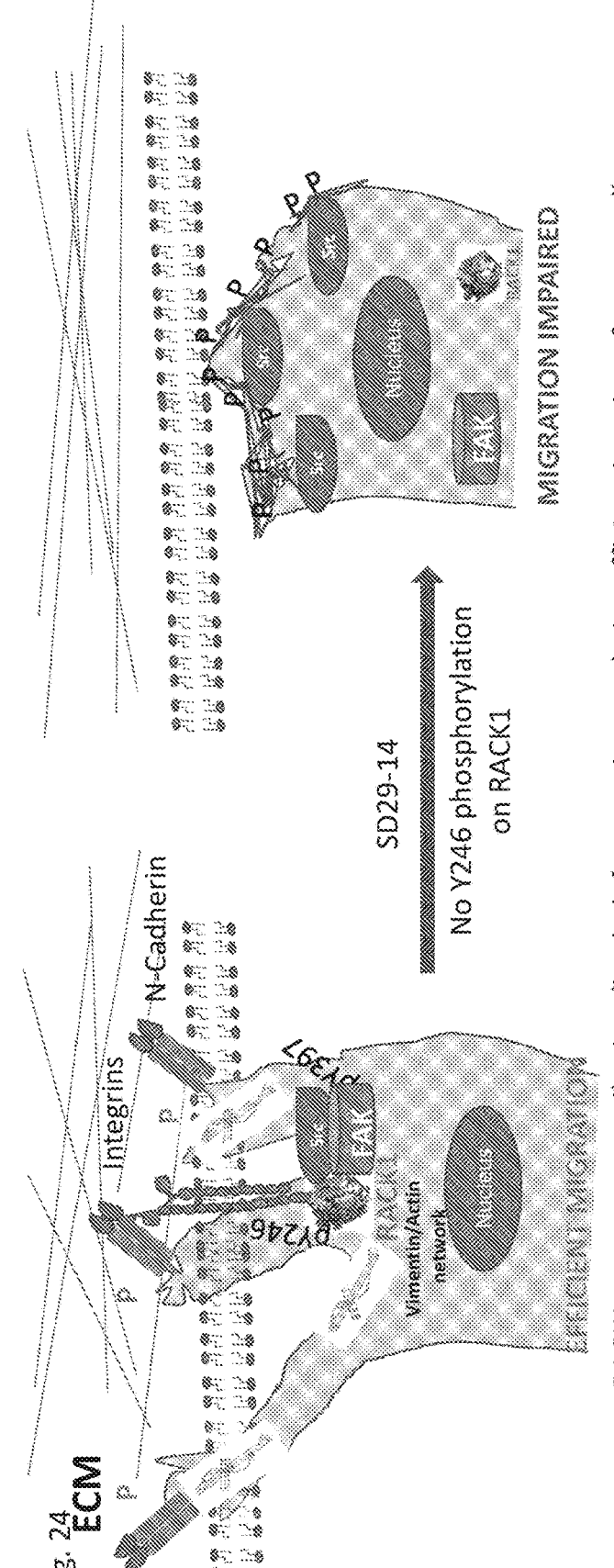

Fig. 24

RACK1 acts as a versatile signaling hub for proteins regulating efficient invasion of cancer cells RACK1 mediates cell spreading by establishing contact with the extracellular matrix (ECM) and ECM protein receptors-integrins, at the focal adhesion sites. Integrin clustering is sufficient to promote the phosphorylation of FAK (Focal Adhesion Kinase) on Tyr-397. This in turn generates a binding site for the Src homology 2 (SH2) domain of Src Family protein tyrosine kinases (Src-family PTKs). The recruitment of Src-family PTKs to FAK is dependent on the initial autophosphorylation of Tyr-397. Phosphorylation of RACK1 on Tyr-246 is required for the binding to the Src. RACK1 is also reported as the substrate of Src for this phosphorylation. Binding of RACK1 to Src is essential to regulate FAK's function. Formation of RACK1$^{Y246}$–Src-cFAK$^{397}$ complex allows targeted phosphorylation of substrates at the focal adhesions and invadopodia by Src causing efficient invasion. Abolition of RACK1 Y246 phosphorylation breaks the complex and Src is free to phosphorylate substrate indiscriminately leading to migration impairment. Over-expression of N-Cadherin is a marker of EMT (Epithelial to Mesenchymal Transition)- the transition is a hallmark of migration. In cells in culture, it is well known that the phosphotyrosine-proteins are highly accumulated at focal adhesions, reflecting the highly specific area of signal transduction. The Stress fibers (Actin-based) has also a major role for migration. The formation of lamellipodia been attributed to a combined role of F-actin (Red rod interior of cells) and associated proteins and EMT marker Intermediate Filament Vimentin (Blue rod shape left image). Vimentin plays an integral role in the lamellipodia formation and polarity maintenance in migrating cells. Vimentin though localized at the invading cells membrane leading edge, disassembly of the vimentin from the leading edge within the lamellipodia towards the cell interior has been shown to be necessary for formation of cellular polarity, leading to an increase in migration. When vimentin filaments were disrupted using a dominant-negative vimentin probe, there was a significant decrease in formation of mature invadopodia (Scheumacher et al., 2010). For simplicity only few Actin and Vimentin complexes in the migration process are depicted in the model.

SEQUENCE LISTING

```
<160> NUMBER OF SEQ ID NOS: 2

<210> SEQ ID NO 1
<211> LENGTH: 14
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: PHOSPHORYLATION

<400> SEQUENCE: 1

Phe Ser Pro Asn Arg Tyr Trp Leu Cys Ala Ala Thr Glu His
1               5                   10

<210> SEQ ID NO 2
<211> LENGTH: 14
<212> TYPE: PRT
<213> ORGANISM: Artificial sequence
<220> FEATURE:
<223> OTHER INFORMATION: Synthetic construct

<400> SEQUENCE: 2
```

-continued

| Phe Ser Pro Asn Arg Tyr Trp Leu Cys Ala Ala Thr Glu His |
|---|
| 1          5              10 |

DRUG INHIBITOR AGAINST MIGRATION AND INVASION OF CANCER CELLS AND METHODS OF TREATING AGAINST METASTASIS OF CANCER CELLS

CROSS REFERENCE TO RELATED APPLICATIONS

This application is a National Stage of International Application No. PCT/US2020/024610, filed Mar. 25, 2020, claiming priority based on U.S. Provisional Application No. 62/823,278, filed Mar. 25, 2019.

INCORPORATION BY REFERENCE OF SEQUENCE LISTING

The content of the electronically submitted sequence listing, file name: A268176_substitute sequence listing as filed.txt; size: 944 bytes; and date of creation: Jan. 27, 2025, filed herewith, is incorporated herein by reference in its entirety.

FIELD OF TECHNOLOGY

Methods pertain to treatment against cancers involving inducing functional inactivity of a protein instrumental in cancer metastasis and invasion. More particularly, methods comprise administering an inhibitor of such a protein, RACK1, in treatment against migration and invasion of cancer cells.

BACKGROUND

Cancer has been identified as a leading cause of deaths worldwide. The leading cause of cancer mortality has been attributed to the migration and invasion (metastasis) of cancer cells to distant organs, but apparently not necessarily attributed to localized cancer.

Long standing efforts to develop effective treatments against cancer are legion. Despite efforts to target the metastasis process of the cancer cells, and despite significant advances in cancer research throughout the decades, development of treatments against cancer still faces serious challenges.

Receptor of activated protein C kinase 1 (RACK1) is a multifaceted scaffold protein. It is a highly conserved intracellular adaptor protein that plays a prominent role in cancer cell invasion and migration that usually lead to the metastasis process. (see, e.g., Li and Xie, Oncogene, 34:1890-1898 (2015); Duff and Long, 2017, Cellular Signaling; 35:250-255 (July 2017): Einhom et al., BioSciences Master Reviews, November 2013, pp. 1-9)). The molecular mechanisms regulating the migration and invasion of cancer cells are well-studied, and the RACK1 protein has been reported to regulate the scaffolding of signaling proteins at the receptors which is found to be particularly important in dynamic processes such as cell migration, cell adhesion and cell spreading (Hermanto et al, 2002). RACK1 has been reported to be a mediator of cell spreading by establishing contact with the extracellular matrix and growth factor receptors at adhesion sites as well (Hermanto et al., 2002).

These processes include several signaling pathways with significant and well-orchestrated cross-talk between cell surface receptors and elements of the cell cytoskeleton.

RACK1 in humans has been reported to regulate cancer cell migration and invasion through different cellular pathways, which include a physical interaction with Src kinase to modulate this regulator of cancer cell migration (e.g., Liliental & Chang; 1998); an interaction with the focal adhesion kinase (FAK) to regulate the polarity and direction-sensing of cancer cells from apical basal to front-rear direction (e.g., Onishi et al., 2007); and promoting the Epithelial to Mesenchymal transition (EMT), which is a process known to promote the migration and invasion of cancer cell (e.g., Lv et al., 2016). Sre is a well-known regulator of cell adhesion, cell spreading and cell migration (e.g., Mamidipudi et al., 2004a). Src activity is inhibited by the binding of RACK1 but loss of RACK1 can prevent the transport of Sre to specific cellular compartments where Sre can function (e.g., Mamidipudi et al., 2004b). RACK1 is also found to regulate the assembly and functioning of the Focal Adhesions which are large dynamic macromolecular assemblies with both mechanical components and cell signaling components in the cancer cell migration process (e.g., Romer et al, 2006; Onishi et al, 2007). Suppression of RACK1 expression disrupts FAK activity, cell adhesion and cell spreading (e.g., Kiely et al., 2009). EMT is an important process during cancer metastasis when epithelial cells lose the apical-basal polarity and cell-cell adhesion and the cells are transformed into invasive mesenchymal cells. RACK1 has been implicated in the EMT and in the invasion process in diverse cancer cells, such as in esophageal squamous cell carcinoma (e.g., Wang et al., 2015); in human glioma (e.g., Lv et al., 2016); in prostate cancers (e.g., Shen et al., 2013); in breast cancers (e.g., Kiely et al., 2016); and in non-small cell lung cancer (e.g., Qu et al., 2017). In addition, the EMT process has been implicated cancer cells exhibiting drug resistance (e.g., Du and Shim 2016).

RACK1 has been reported as a regulator of cancer cell migration and invasion, which are prerequisites for the metastasis process.

RACK1 has been implicated in several pathways that lead to cancer cell migration and invasion.

Developing inhibitor compound(s) effective to induce functional inactivation of RACK1 in cancer cell metastasis and methods using such compounds would be significant advances in metastasis treatment.

SUMMARY

We have discovered certain compounds inhibit the functional expression of RACK1 in cancer cell lines, and such compounds(s) as drugs can be effective in preventing the cancer cell metastasis.

Here we develop an application of an inhibitor compound for RACK1 protein for administering in a treatment against cancer cell migration and invasion—a leading cause(s) of metastasis of cancer cells.

A method for treating against cancer comprises administering a compound represented by any of formula (1), (2), and/or (3) to cancer cells, such as to disrupt cell migration and inhibit cancer cells from invasion of other tissue (metastasis of the cancer). The administration can be in vivo or in vitro, and therefore administration can be to cancer cells, to a cancerous tumor, or to a patient in need of treatment.

A method for treating against a cancer comprises administering a compound, a tautomer, or a pharmaceutically acceptable salt thereof, in an amount effective for inhibiting metastasis of the cancer cells, wherein the compound is represented by the formula (1):

3 wherein each $R_1$ represents a halogen atom. Each $R_1$ is independently selected from the group consisting of bromo, chloro, fluoro and iodo.

In another of its aspects, in a method each $R_1$ is the same.

In another of its aspects, in a method at least one $R_1$ represents chloro.

In another of its aspects, in a method each $R_1$ represents chloro.

In any of its aspects, in a method the cancer is a cancer in which human RACK1 is a positive regulator in cancer metastasis.

In any of its aspects, in a method the cancer comprises breast cancer.

In any of its aspects, in a method the cancer comprises gliobastoma.

A compound(s) represented by formula (1), (2) and/or (3) as an active ingredient (drug) is effective in treating against diverse cancer metastasis. Administering such a compound (s) can silence the RACK1 protein by rendering it functionally inactive as a positive regulator in cancer metastasis. In cancers in which RACK1 is a positive regulator, the process of metastasis is said to require a functionally active RACK1 protein which is phosphorylatable a key residue(s).

Thus, in another of its aspects, a method comprises administering a compound represented by formula (1), (2) and/or (3) to cancer cells to inhibit a key tyrosine phosphorylation residue(s), namely block or impair the phosphorylation of such residue(s). Based on present data, one such residue is apparently the Y246 residue in RACK1 (human).

In another of its aspects, a method comprises administering a compound represented by formula (1), (2) and/or (3) to cancer cells to inhibit the key regulator protein N-cadherin for the focal adhesion anchoring to the extracellular matrix.

In a further aspect, a method comprises administering a compound represented by formula (1), (2) and/or (3) to cancer cells to inhibit the development or formation of filopodia and lamellipodia in cancer cells.

In a further aspect, a method comprises administering a compound represented by formula (1), (2) and/or (3) to cancer cells for at least impairing vimentin function, e.g., essentially interfering with and inhibiting vimentin expression and/or function, to combat cancers by inhibiting, retarding, or at least suppressing metastasis and tumorigenesis, such as epithelial-derived cancers that are associated with expression of vimentin, especially with over expression of vimentin.

Thus, another aspect involves administering an amount of a compound represented by formulae (1), (2) and/or (3) effective to induce functional inactivation of RACK1 (human) to inhibit the spread of a cancer, such as by arresting, inhibiting, impairing, suppressing, or retarding cancer cell proliferation, migration and thus metastasis. In other words, in one of its aspects, RACK1 protein (human) is rendered functionally inactive by administering an effective amount compound(s) according to formulae (1), (2) and/or (3).

A cancer inhibitor composition comprising a compound, a tautomer, or a pharmaceutically acceptable salt thereof for inhibiting metastasis of cancer cells in which RACK1 functions as a positive regulator for cancer cell migration and metastasis, wherein the compound is represented by the formula:

wherein each $R_1$ is independent of the other and represents a halogen atom selected from the group consisting of bromo, chloro, fluoro and iodo. The cancer inhibitor composition can further comprise a carrier and/or additional ingredients in formulating such a composition for administration.

BRIEF DESCRIPTION OF THE FIGURES

FIG. 5 shows in a series of photomicrographs in a comparison against a control that a low concentration of a representative compound (SD 29-14 is also effective in blocking migration structures in 72 h grown MCF-7 cells.

FIGS. 9 and 10 represent how SD-29-14 treatment to functionally inactivate RACK1 leads to the inhibition of migration (FIG. 9) and invasion (FIG. 10) of U251 cells.

FIG. 11 presents side-by-side photomicrographs to compare a control versus representative dosing of U251 cells with a representative compound (SD 29-14) that shows the representative compound inhibits lamellipodia/filipodia co-localization of RACK1 with Extracellular Matrix (ECM) protein LamB1 in U251 cells.

FIGS. 14 and 15 relate to showing an evaluation of the effect of SD29-14 induced functional inactivation of RACK1 on the FAK phosphorylation. The drug (e.g., SD 29-14 as a representative compound) was used in treating against breast cancer cells—MCF7 (FIG. 14) and against U251—glioblastoma (FIG. 15).

FIG. 16 shows the migration of U251 cells through matrigel without any SD 29-14 present.

FIG. 20 shows localized F-actin foci helps develop stress fiber based directional filopodia development whereas administration of a representative compound (SD 29-14) prevents organized filopodia development in U251.

FIG. 21 shows inhibition of vimentin (EMT marker) can prevent invasiveness of cancer cells (U251). FIG. 21 shows the effects when a representative compound administration is at 100 uM concentration.

FIG. 22 shows inhibition of vimentin (EMT marker) can prevent invasiveness of cancer cells (U251). FIG. 22 shows the same effects as in FIG. 21 when a representative compound administration is at 10 uM concentration.

FIG. 23 illustrates a structural model showing SD 29-14 and RACK1 (human).

FIG. 24 illustrates a proposed model based on reports depicting the role of RACK1 protein in the scaffolding complexes with key regulator proteins for migration through the development of lamellipodia/filopodia/invadopodium.

DETAILED DESCRIPTION

Figure 1:
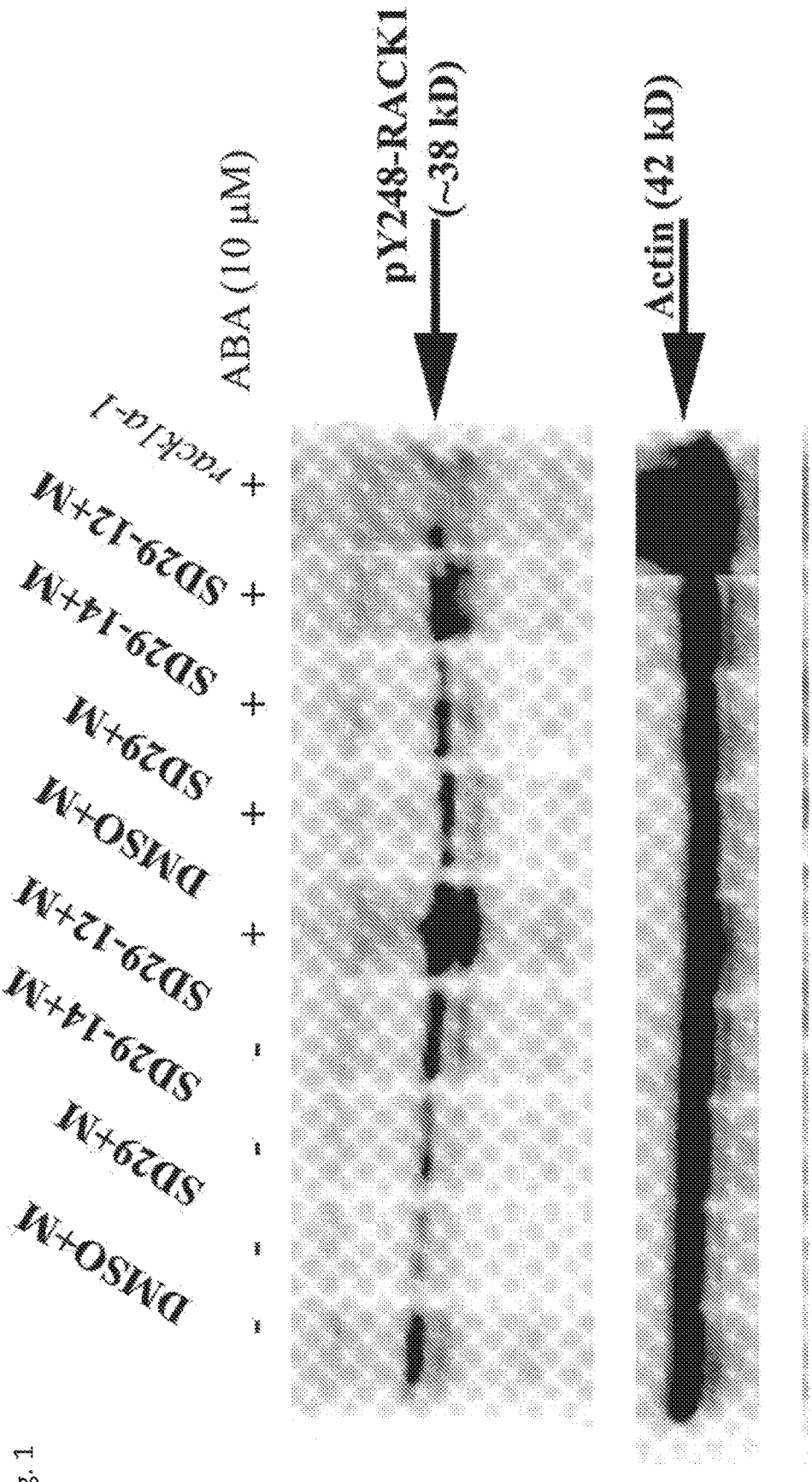
FIG. 1 shows RACK1 functional inhibitor compounds inhibit stress hormone induced RACK1A Y248 phosphorylation.

A method for treating against cancer comprises administering a compound represented by any of formula (1), (2), and/or (3) to cancer cells, such as for disrupting cell migration and inhibiting invasion (metastasis of the cancer). The administration can be in vivo or in vitro, and therefore administration can be to cancer cells, to a cancerous tumor, or to the patient.

In one of its aspects, a method comprises administering a compound represented by formula (1), (2) and/or (3) to cancer cells to inhibit a key tyrosine phosphorylation residue(s), namely block or impair the phosphorylation of such residue(s).

In another of its aspects, a method comprises administering a compound represented by formula (1), (2) and/or (3) to cancer cells to inhibit the key regulator protein N-cadherin for the focal adhesion anchoring to the extracellular matrix (ECM).

In a further aspect, a method comprises administering a compound represented by formula (1), (2) and/or (3) to cancer cells to inhibit the development of filopodia and lamellipodia in cancer cells.

In a further aspect, a method comprises administering a compound represented by formula (1), (2) and/or (3) to cancer cells for at least impairing vimentin function, e.g., essentially interfering with and inhibiting vimentin expression and/or function, to combat cancers by inhibiting, retarding, or at least suppressing metastasis and tumorigenesis, such as epithelial-derived cancers that are associated with expression of vimentin, especially with over expression of vimentin.

An aspect of the methods involves administering an amount of a compound represented by formulae (1), (2) and/or (3) effective to induce functional inactivation of RACK1 to inhibit cancer cells, such as by arresting, inhibiting, impairing, suppressing, or retarding their proliferation, migration and thus metastasis.

A method for treating against a cancer metastasizing and invading surrounding tissue involves administering one or more of the compound(s), and/or tautomer(s), and/or a pharmaceutical salt(s) thereof to a host in need of treatment, wherein the compound is represented by the formula (1):

wherein each $R_1$ is independent of the other and each represents a halogen atom.

Accordingly, in an aspect of a method for treating, inhibiting or suppressing a cancer, each $R_1$, independent of the other, represents a halogen atom selected from the group consisting of bromo, chloro, fluoro and iodo.

In another embodiment, a compound represented by formula (2), which is an example of a compound represented by formula (1), a tautomer thereof, or a pharmaceutically acceptable salt thereof, is administered to a host in need of treatment against a cancer metastasizing and invading surrounding tissue to at least effect inhibition or suppression, if not block, migration and invasion (metastasis) of a cancer, wherein the compound represented by formula (2) is:

wherein each X is the same and represents a halogen atom (bromo, chloro, fluoro, or iodo).

In a further embodiment, a compound, denoted SD-29-14, its tautomer or a pharmaceutically acceptable salt is administered to a host in need of treatment against a cancer metastasizing and invading surrounding tissue to at least effect inhibition or suppression, if not block, migration and invasion (metastasis) of the cancer, wherein the compound is represented by formula (3):

7

SD 29-14 of formula (3) is a compound of formula (1) and a compound of formula (2).

A compound(s) represented by formulas (1), (2) and (3) is preferably administered in treating against, or at least inhibiting, suppressing or retarding a cancer in which RACK1 acts as a positive regulator of cancer cell migration (metastasis and invasion).

One of the preferred compounds has a chloro substituent on at least at one of meta positions of the phenyl ring, and more preferably the compound has a chloro substituent at both meta positions.

In formulae (1), (2) and (3), by preference the azole moiety is shown with an —SH substituent and it will be appreciated tautomers in which there is a =S moiety instead may be used.

A present method for treatment unexpectedly shows at least a marked impairment of a cancer of the kind described herein. Our methods provide a treatment that interferes with the RACK1 protein functioning in the spread of such cancers to thereby block, or at least impair, inhibit, or suppress the spread of such cancers (e.g., growth, invasion and metastasis).

A compound according to formula (1), (2) and/or (3) herein can function as a RACK1 inhibitor, and when administered the at least one compound of a formulae herein is believed to target and bind to one or more of the RACK1 functional sites to produce a modified RACK1 to inhibit cancer cell growth, proliferation, migration and metastasis.

In the present context, in a present method, administering an amount of a compound or formulae (1), (2) and/or (3), or a tautomer or pharmaceutically acceptable salt thereof, is in an amount effective for at least inhibiting a cancer of the type as described herein. A RACK1 inhibitor as described herein interferes with site(s) (sometimes called pocket(s)) in the RACK1 of interest, e.g., human RACK1, so that the RACK1 as modified by a compound of a formulae herein is inhibited. The inhibition disrupts the RACK1 (an induced functional inactivation) and interferes with the replication and spread of a cancer of the kind described herein. A site targeted by the RACK1 inhibitor includes the Y246 site human RACK1 (which we have determined appears to correlate with the Y248 site in plants, such as *Arabidopsis*). Other sites affected in human RACK1 may additionally include the K273 pocket and similar sites. In vitro data are consistent with the induced inactivation of the Y246 site being related to interfering with or preventing the human RACK1 Y52 site from being phosphorylated.

Based on our discoveries, within a cancer environment, since RACK1 (mammalian RACK1, e.g., human) acts as a dynamic bub of signaling proteins regulating cell migration/invasion/metastasis, its inhibition or inducing its functional deactivation with a compound represented by formula (1), (2), or (3), or a tautomer or pharmaceutically acceptable salt thereof, in cancer metastasis would be an effective treatment against metastasis.

Src kinase association is a key for metastasis (Chang et al, J Biol. Chem., 276:20346-20356 (2001)). Y246 phosphorylation of human RACK1 is required for it to interact with Src protein tyrosine kinase, so a compound (e.g., SD 29-14 of a formula herein) will adversely affect Src dependent phosphorylation of FAK. Src-dependent FAK phosphorylation is required for focal adhesion turnover and cell migration.

Inhibiting RACK1 from forming a complex with integrin and FAK can inhibit cell migration. RACK1 Y52 phosphorylation can occur when the complex is stably formed. However, functionally inactivating RACK1 (e.g., inhibiting RACK1 Y246 phosphorylation) will block or at least inhibit the complex from forming.

Vimentin is a cytoskeletal protein and is a type III intermediate filament (IF) protein. Its elevated expression has been associated with increased metastasis, reduced survival, and poor prognosis for diverse cancers (e.g., Wang et al., Cancer Biol. & Ther., 16 (4): 528-540 (2015), noting cancers described; Qu et al., Int. J. Clin. Exp. Med., 10 (6): 9019-9028 (2017)). Vimentin expression has been related to mediating cellular migration and lamellipodia. Its high or extensive or over expression (upregulation) has been associated with EMT. Vimentin has therefore been used as a marker of EMT in metastasis. It has been reported vimentin binding stably to FAK is RACK1 dependent (Dave et al., J. Biol. Chem. 288 (42): 30720-30733 (2013)). Vimentin has been associated with development, elongation and maturation of invadopodia, which are specialized protrusions that when fully developed breach the cellular "basement membrane" leading to development of lamellipodia and a metastatic cancer cell becoming mobile and polarized (Kidd et al., Transactional Rev., Am. J. Resp. Cell. Mol. Biol., 50 (1): 1-6 (2014); Schoumacher et al., J. Cell Biol., 189 (3): 541-556 (2010)). Elevated vimentin-expression has been associated with increased tumor invasiveness. Vimentin, in particular elevated/over/high vimentin expression, appears to be a potential anti-cancer target ((Lahat et al., PLosOne, 5 (4): 1-19 (2010); McInroy et al., Biochem. Biophys. Res. Comm., 360 (1): 109-114 (2007)). Vimentin has been identified as a target for possible antimetastatic therapy with RNAi for nasophryngeal carcinoma (NPC) with vimentin impairment, e.g., depletion, apparently inhibiting motile and invasive behaviors for epithelial-derived NPC (Wang et al., Mol. Cellular Biochem., 438 (1-2): 47-57 (2018)). Vimentin has been described as a possible target for interrupting the metastatic cascade in tumorigenesis to inhibit lung cancer metastasis. (Kidd et al., Transactional Rev., Am. J. Resp. Cell. Mol. Biol., 50 (1): 1-6 (2014)).

Mutation of Y248 inhibited RACK1 (plant) interaction capability with other proteins (Sabila et al (2016) and Kundu et al. (2013)).

Our in vitro data are consistent with unstable RACK1 (human), from its induced functional inactivation (from administering a compound(s) of formulas (1), (2) and/or (3)), not being able to bind (associate) with vimentin.

Our in vitro data show a representative compound according to our formulas (1), (2) and (3) can force an induced functional impairment (inactivation) of RACK1 that interferes with vimentin expression (or over expression) to inhibit progression of cancer metastasis and invasiveness or towards cancer metastasis and invasiveness. Interfering with vimentin or its expression can disrupt, if not block, consequent development of lamellipodia and the cellular polarity that are associated with motility and invasiveness that are characteristic of cancer metastasis.

In vitro data support compromising metastasis by silencing (knocking down), or at least inhibiting vimentin expression, which is a form of forced vimentin dysfunction, to block, to silence or at least impair the development of invadopdia as well as the consequent formation of lamellipodia by administering an effective amount of a compound represented by formula (1), (2) and/or (3) to cancer cells, tumor, or patient in need of treatment.

The inhibition or impairment of RACK1 reportedly affects association of vimentin and FAK (focal adhesion kinase). The association has been reported to be a step in lamellipodia formation. As disclosed elsewhere herein, it has been reported vimentin stably associating or binding to FAK is RACK1 dependent (e.g., Dave et al., J. Biol. Chem. 288 (42): 30720-30733 (2013)). Suppression of RACK1 expression disrupts and at least reduces, suppresses or inhibits, if not blocks, FAK activity and cell spreading (e.g., Kiely et al., J. Biol. Chem., 284 (30): 20263-20274 (2009)). Disrupting the formation of the pTyr397 FAK residue apparently interferes with the association of FAK and vimentin, since complete loss-of-FAK phosphorylation (pY397 FAK) has been reported as causing a near complete loss of FAK association with vimentin, with vimentin reported as required for FAK activity (e.g., Havel et al., Oncogene, 34 (15): 1979-1990 (Apr. 9, 2015)).

The RACK1 Y52 residue is another residue involved with FAK activity. Forming a complex of RACK 1 with IGF-I and Integrin, with FAK phosphorylated at Y397 which stabilizes the complex, wherein IFG-I stimulates c-Abl activity with RACK1 being phosphorylated at Y52, with FAK then being dephosphorylated at Y397 is reported to promote cell migration (Kiely et al. 2009).

Accordingly, disrupting, interfering and/or blocking or preventing, the formation of a phosphorylated RACK1 (human) in accord with a method herein interferes with and inhibits phosphorylating the Tyr397 residue of FAK, which would inhibit formation of a complex including RACK1, FAK and vimentin, which would additionally interfere with stimulating phosphorylating the RACK1 Y52 residue. (The formation of phosphorylated RACK1 refers to RACK1 having a phosphorylated Y246.) This apparently through conformational changes leads to or at least contributes to inhibited (e.g., suppressed or reduced), if not blocked, cell migration, whereas allowing phosphorylation of the RACK1 Y52 residue in the complex has been reported by Kiely et al. (2009) to stabilize the association of FAK and RACK1 that is reported to be involved with FAK activity related to spread of a cancer.

RACK1 mediates effects on cell migration apparently through regulation of focal adhesion (FA) assembly by promoting focal adhesion kinase (FAK) activation downstream of integrin clustering and adhesion. Recent studies in mouse fibroblasts suggest that vimentin may stabilize focal adhesion assembly and regulate FA contact size in response to shear stress. These focal adhesion assemblies are dynamic macromolecular assemblies that link cells to the extracellular matrix. FAK is a major tyrosine kinase protein concentrated at these focal adhesion assemblies. Extracellular matrix engagement and integrin assembly promote FAK phosphorylation, which further recruits and phosphorylates other proteins at FAs to promote cytoskeletal rearrangement and cell migration. FAK has been extensively studied in cell migration, angiogenesis, and cardiac morphogenesis. It has been reported that a trimolecular complex between RACK1, vimentin, and FAK is stimulated by proangiogenic factors in three-dimensional invading cultures.

Our in vitro data are consistent with RACK1 being needed to stabilize the complex between vimentin and FAK, consistent with knockdown of RACK1 resulting in poor invasion responses and at least attenuated FAK activation, and consistent with inhibiting such a complex from forming by inducing functional inactivation of RACK 1 against phosphorylation (e.g., at the Y246 residue).

Our in vitro data are consistent with administration of a representative compound according to formulae (1), (2) and/or (3) (e.g., SD-29-14), or a tautomer or pharmaceutically acceptable salt, interferes with (e.g., inhibits or disrupts) and/or blocks localization and phosphorylation of Tyr397-FAK to the Focal Adhesions (doublet) in cancer cells such as MCF-7 cells.

Our in vitro data are consistent with administering compound(s) according to formula (1), (2) and/or (3), or their tautomers or their pharmaceutically acceptable salts, to treat a cancer by at least inhibiting progression of cancer metastasis and invasiveness or inhibiting progression towards cancer metastasis and invasiveness.

Dysregulation of or silencing a receptor of activated protein kinase A (RACK1), e.g. inducing its functional inactivation, can positively or negatively affect cancer cell migration and metastasis (e.g., Li et al., Oncogene, 34:1890-1898 (2015); Cheng, Cancer Res. 75 (18): 3832-3841 (2015)).

In one of its aspects, a method comprises administering a compound represented by formula (1), (2) and/or (3), or its tautomers or pharmaceutically acceptable salts, to cancer cells to inhibit a key tyrosine residue, such as in RACK1 (human), to block or impair the residue from being phosphorylated, and which in vitro data is consistent with inhibiting RACK1-mediated modulation of Src kinase activity in cancer cells. When the tyrosine residue is phosphorylated, the development of FAK/Integrin/Src kinase complex formation to assemble focal adhesion structure for cancer cell migration and invasion (metastasis) has been reported. RACK1 is reported in connection with RACK1-mediated modulation of Src kinase activity in Duff et al., Cellular Signalling, 35:250-255 (2017). RACK1 is also reported to be an indispensable component in a so-called direction sensing pathway that includes the integrin effector FAK and PDE4D5. Li et al., Oncogene, 34 at 1895; Serrels et al., Curr. Biol. 20:1086-1092 (2010).

In another of its aspects, a method comprises administering a compound represented by formula (1), (2) and/or (3), or its tautomers or pharmaceutically acceptable salts, to cancer cells to inhibit or suppress a key regulator protein N-cadherin for the focal adhesion anchoring to the extracellular matrix. The N-cadherin expression is reported as a hallmark for the epithelial-mesenchymal transition (EMT) process that is associated with cancer metastasis and invasiveness, in which the expression of a form of EMT implicated with the migration and invasion (metastasis) of cancer cells (e.g., Lamouille et al., Nat. Rev. Mol. Cell Biol., 15 (3): 178-196 (March 2014)). EMT is a process in which cells transition from an epithelial phenotype to a mesenchymal phenotype and become more invasive and acquire the ability to migrate (Wang et al., Cancer Biol. & Therapy, 16 (4): 528-540 (2015)). In general, in initial step(s) of the EMT transition, epithelial cell-cell contacts-adherens junctions, desmosomes and so-called gap junctions—are disassembled and cell polarity is typically lost. Cellular epithelial genes are repressed while mesenchymal gene expression is activated. Epithelial actin architecture is said to be reorganized in this transition. The cancer cells acquire motility and invasive capability with lamellipodia, filopodia and invadopodia formation in the cancer-related form of EMT. Blocking expression of RACK1 (including downregulating, or at least suppressing, if not silencing, RACK1) can promote apoptosis and greatly inhibit cell proliferation, migration and invasion ability of human glioma cells (Lv et al., Int'l J. Environ. Res. and Public Health, 13:1021 (2016)) with the suppressed migration and invasion associated with the inhibited expression of EMT markers, such as N-cadherin.

In a further aspect, a method comprises administering a compound represented by formula (1), (2) and/or (3), or its tautomers or pharmaceutically acceptable salts, to cancer cells to inhibit the development of filopodia and lamellipodia in cancer cells. RACK1 has been implicated in the actin polymerization process to support development of filopodia and lamellipodia (Quadri, Microvasc Res., 83 (1): 3-11 (January 2012)).

Our in vitro data are consistent with a representative compound (e.g., SD-29-14) according to formulae (1), (2) and/or (3) blocking the filipodia development (formation) needed for migration of gliobastoma cells (U251 cells) and for migration of breast cancer cells (MCF-7 cells).

Our in vitro data are consistent with blocking being achievable against gliobastoma cells (U251 cells) and against breast cancer cells (MCF-7 cells) when the representative compound is administered in an effective concentration, including administration in a low concentration (low dosing).

Our in vitro data are consistent with administration of a representative compound(s) blocking stress fiber development in the lamellipodia of glioblastoma cells (U251).

Administering a compound(s) represented by formulae (1), (2) and/or (3) can be effective in preventing migration and invasion processes, such as regulating the integrin anchoring through the disruption of the focal adhesion assembly, inhibiting a key anchoring and EMT protein N-cadherin, and/or by disrupting the actin-based migration appendage development are considerations in support inasmuch as cancer metastasis apparently involves such pathways.

In vitro data relating to representative cancers supports administration of the compound(s) of the formulas herein are effective in blocking, or at least inhibiting, metastasis in diverse cancers of the type described herein.

Data show that a compound(s) as described herein disrupts and interferes with RACK1 protein (human) and that such compound(s) can be administered to at least inhibit proliferation and spread of a cancer of the kind described herein. The efficacy of RACK1 impairment as a means for inhibiting, or at least suppressing, retarding, impairing, or repressing cancers in which RACK1 is a positive regulator is borne out by the data from our in vitro testing with such representative cancer cell lines as breast cancer (MCF7) and brain cancer (glioblastoma (U251)).

RACK1 is known to be a positive regulator of cancer cell invasion and migration but in few cancer instances it can act as a negative regulator of cancer cell migration and invasion such as in gastric cancer. Chen et al., 2015. Loss of RACK1 Promotes Metastasis of Gastric Cancer by Inducing a miR-302c/IL8 Signaling Loop Cancer Res. (75) (18) 3832-3841 (2015) and e.g., Duff et al., Cellular Signaling, 35:250-255 (2017); Li et al., Oncogene, 34:1890-1898 (2015); Lv et al., Int. J. Environ. Res. Public Health, 13:1021-1036 (2016); Mamidipudi et al., Oncogene, 26:2914-2924 (2007). By preference, a compound represented by formula (1), (2) and/or (3), or its tautomer or pharmaceutically acceptable salt, is administered against a cancer in which RACK1 acts as a positive regulator of cancer cell migration. Cancers in which RACK1 acts as a positive regulator have been described (e.g., Duff et al. (2017); Lv et al, (2016), among others). Examples of such cancers include adenocarcinoma, breast cancer, colon cancer (Mamidipudi et al., Oncogene, 26:2914-2924 (2007)) glioma cells (Peng et al., Oncol. Rep. 30:2195-2202 (2013) such as human glioma (including glioblastoma), epithelial ovarian cancer (Lin et al., Int'l J. Oncology, 44 (4): 1252-1258 (2014), esophageal squamous cell carcinoma (Wang et al., Cancer Biol. & Therapy, 16 (4): 528-540 (April 2015), hepatocellular carcinoma (HCC) (Ruan et al., J. Clin. Invest., 122 (7): 2554-2566 (2012); Wang et al., Oncology Letters, 9:2767-2770 (2015)), lung cancer (for example, non-small cell lung cancer (NSCLC) (Choi et al., Oncotarget, 6 (6): 4451-4466 (2015)); neuroblastoma (Lu et al., Oncol. Rep. 27:1646-1652 (2012)), pulmonary adenocarcinoma, and prostate cancer (Shen et al., Molecular Medicine Reports, 8:999-1004 (2013)), among others. We used a breast cancer cell line (MCF-7) and glioblastoma cell line (U251) as representatives of such cancers.

Compounds in accordance with a formula herein can be prepared by adapting the following synthesis.

R: KOH, S: EtOH, rt; overnight, rt; cooled
R: $N_2H_4$—$H_2O$, S: $H_2O$, 6 h, reflux, cooled
R: HCl, S: $H_2O$, acidify wherein each X, independent of the other, represents a halogen atom.

An exemplary method for synthesizing a representative compound, known as SD-29-14, is:

SD-29-14
3,5-dichlorobenzohydrazide

R: KOH, S: EtOH, rt; overnight, rt; cooled
R: $N_2H_4$—$H_2O$, S: $H_2O$, 6 h, reflux, cooled
R: HCl, S: $H_2O$, acidify methanedithione -continued 4-amino-5-(3,5-dichlorophenyl)-1,2,4-triazole-3-thiol Other syntheses can be adapted from Molecules, 6:815-824 (2001).

Compounds of a formula (1), (2) and (3), can also be synthesized by adapting the following synthesis. The hydrazide (0.04 mol) and KOH (0.04 mol) in 50 cm³ MeOH is treated with $CS_2$ (0.04 mol), and the mixture is stirred for 16 h at room temperature. Diethyl ether (50 cm³) is added, and the precipitated solid is filtered, washed with ether, and vacuum-dried at 78° C. in a drying pestle. The potassium salts of substituted dithiocarbazinic acids are used for the next step without further purification. The potassium salt of the substituted dithiocarbazinic acid (0.02 mol) and hydrazine hydrate (0.04 mol) in 2.0 cm³ water are heated under reflux with stirring for 0.5-1.5 h. The color of the reaction mixture changes to green with the evolution of hydrogen sulfide, and a homogeneous solution is formed in about a half an hour. When evolution of hydrogen sulfide ceases (lead acetate test), the reaction mixture is diluted with 50 cm³ cold water and acidified with 6 N hydrochloric acid. The precipitated solid was filtered, washed with cold water, and recrystallized from aqueous EtOH.

In a present method, a host is one in need of treatment against a cancer. It will be appreciated that the method can be practiced with cancer cells in vivo or in vitro. The host can comprise a mammal (patient, e.g., human) in need of treatment against a cancer. By preference, the cancer to be treated is one in which RACK1 can act as a positive regulator of cancer cell migration.

Various routes of administration are possible with a present method. Administration can be orally, by injection, or by intravenous drip. For example, the RACK1 inhibitor can be formulated in solid dosage form, such a capsule, tablet or the like, or can be formulated as a suspension or as another non-solid dosage form, such as a liquid or syrup. Administration can be directly at the cellular level, to cancerous growths (e.g., tumors), or systemically to the patient, such as intravenously, or bucally as examples. The administration can comprise administering a present compound, a tautomer thereof, and/or a pharmaceutically acceptable salt thereof as the active ingredient(s).

An anticancer composition (dosage form) can comprise a compound(s) of any of formulae (1), (2) and/or (3) formulated with a carrier suitable for the selected method of administration. For example, the compound(s) can be formulated in solid dosage form, such a capsule, tablet or the like, or can be formulated in a liquid suitable for administration orally or by injection (including, e.g., intravenous drip etc.)

An anticancer composition (dosage form) can comprise a compound(s) according to any of formulae (1), (3) and/or (3) formulated with a pharmaceutically acceptable excipient(s) and the like. Illustrative excipients are described in Remington, The Science and Practice of Pharmacy, 20th edition (2000), as an example. A salt of a compound can be used. Illustrative pharmaceutically acceptable salts are described in Remington at pages 703-711 as an example, with a hydrohalide, such as a hydrochloride, being an illustrative example.

A compound represented by any of formulas (1), (2) and (3) herein exhibits an improvement in inhibiting migration and invasion of a cancer, such as a cancer in which RACK1 acts as a positive regulator of cell migration, as compared to a compound (SD-29) in which the phenyl ring is only mono-substituted (fluoro) at the para-position.

(SD 29)

For example, the results are surprisingly better for a representative compound (SD 29-14).

Our in vitro data show the efficacy using the SD-29-14 compound for treating against a cancer in which human RACK1 acts as a positive regulator of cell migration even when the concentration is lowered (such as to 10 uM), and apparently in a dose dependent way, and is effective in inhibiting, suppressing, retarding, or at least stalling migration of such cancer cells and invasion (metastasis) thereof.

The crystal structure of the model plant RACK1A protein has been elucidated and based on the structure has identified the tyrosine 248 as the key functional residue of RACK1 protein (Ullah et al., Protein Science, 17:1771-1780 (2008)). The phosphorylation of Y248 in plants is a prerequisite for the homo-dimerization of RACK1A proteins and to interact with diverse signaling proteins (Kundu et al., 2013; Sabila et al., 2016).

Based on our present work, Y246 of non-plant RACK1 (e.g., human RACK1) is equivalent to Y248 in plants. (FIG. 23 illustrates a proposed docking model re Y246.)

The complete disclosures of all patents and literature referenced herein are incorporated herein by reference.

FIG. 1 shows RACK1 functional inhibitor compounds inhibit stress hormone induced RACK1A Y248 phosphorylation. The results of lab experiment establish the compounds identified by in silico screen to prevent RACK1 Y248 phosphorylation can inhibit RACK1 Y248 phosphorylation and confirm their utility in their application in RACK1 mediated cellular pathways. Y248 phosphorylation has previously been identified as a key event needed for RACK1 mediated scaffolding activities by regulating protein-protein interactions in plants. The corresponding residue in human RAKl is also a key requirement for scaffolding activities needed at the receptor level during the invasion and migration of cancer cells. Here lane 5 clearly shows that with stress hormone present, the Y248 residue of RACK1A protein gets highly phosphorylated, while the inhibitor compounds (SD 29 and SD 29-14) prevents Y248 phosphorylation to the control level; rather keeps the level near the basal level (without the stress hormone). For instance, instead of inhibiting stress hormone-based inhibition of Y248 phosphorylation, other compounds (SD 29-12) can stabilize the protein by maintaining Y248 phosphorylation in response to the stress hormone. As a control, the experiment used protein from a genetic knock-out of RACK1A, and the plant did not show any Y248 phosphorylated band as it lacks the RACK1A protein. The knock-out plant did maintain both the RACK1B protein and the RACK1C protein, but the antibody was raised to detect the RACK1A Y248 phosphorylation only.

As to FIG. 1, since RACK1 is a regulator of plant stress hormone Abscisic acid (ABA) (Guo et al., 2009), one-week old *Arabidopsis* seedlings were treated with 10 uM of ABA in the presence/absence of the inhibitor compounds for 12 hours in a growth chamber (overnight) at 22 C mostly in the night dark. Lysates isolated in buffer (Cell Signaling, MA) supplemented with plant protease inhibitor (Sigma-Aldrich), Protein Tyrosine phosphatase inhibitors (Santa Cruz Biotechnology, TX), and N-Ethylamaleimide (Sigma-Aldrich) at 25 mM to inhibit de-sumoylation. Twenty five microgram of proteins were loaded on the BioRad's 4-12% precast polyacrylamide gel, transferred to a nitrocellulose membrane and then blocked with 5% Bovine Serum Albumin (BSA) for one hour, washed and incubated with the an antibody (1:100 dilution) to detect phosphorylated Y248 residue of RACK1A protein which was raised using the epitope: FSPNR{pTYR}WLCAATEH (SEQ ID NO: 1) (Genscript, Piscataway, NJ, USA). To make it specific to RACK1A pY248, it was raised by adsorbing against the RACK1A non-phosphorylated antigen and to a peptide antigen with sequence FSPNRYWLCAATEN (SEQ ID NO: 2) specific for the *Arabidopsis* RACK1B and RACK1C proteins). A rabbit secondary antibody (1:5000) was used. BIORAD's Clarity ECL substrate was used to visualize the bands. The lower panel shows the same membrane stripped in stripping buffer and then blotted with an *Arabidopsis* actin antibody to show the loading control. The loading control indicates almost uniform amount of protein loading in each lane.

Data are consistent with the Y246 residue in RACK1 (non-plant, e.g., human) being equivalent to the Y248 residue in plant RACK1 (e.g., *Arabidopsis*).

Figure 2:
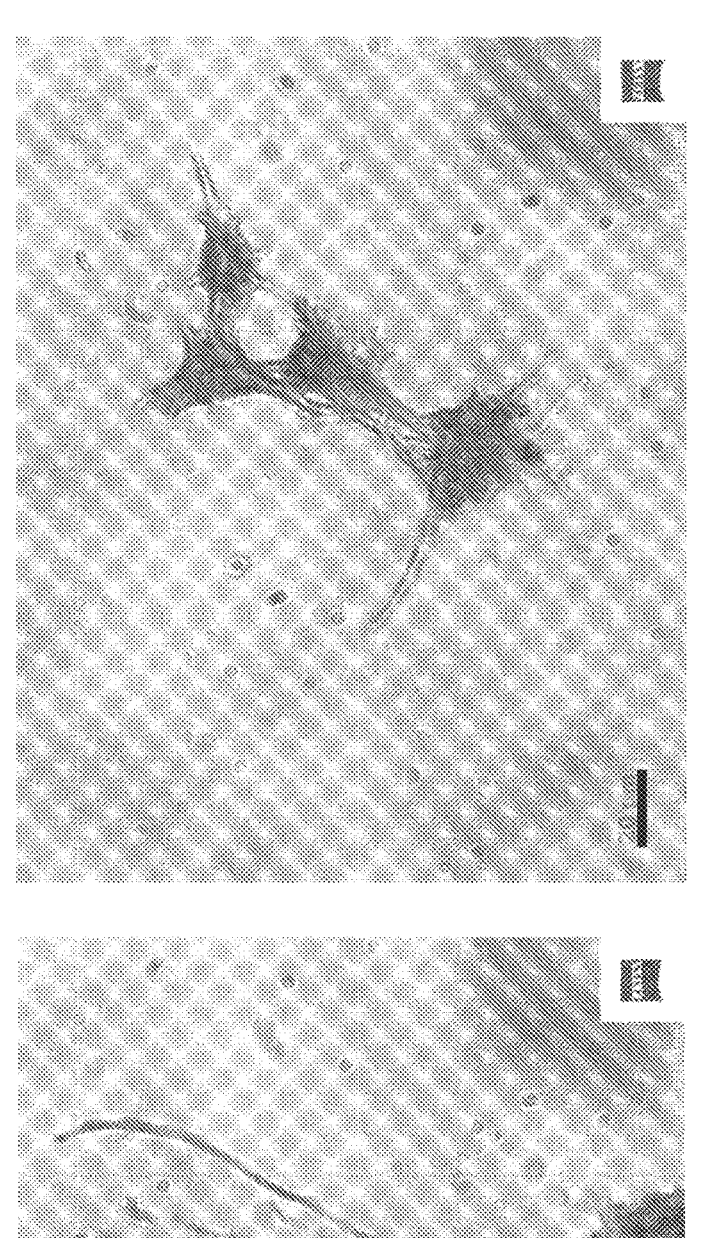
FIG. 2 shows in side-by-side photomicrographs that a representative compound (SD 29-14) blocks filipodia development needed for migration in the representative cancer cells (U251 cells glioblastoma (brain cancer).

FIG. 2 shows in side-by-side photomicrographs that a representative compound (SD 29-14) blocks filipodia development needed for migration in the representative cancer cells (U251 cells (glioblastoma-brain cancer). About 1×10^5 Glioblastoma cells (U251) treated with DMSO or SD 29-14 for 48 h were resuspended in serum free MEM media and were then plated on 1:6 diluted (with serum free media) matrigel (Basement membrane mimic) in the presence of Transforming Growth Factor-TGF (PeproTech. Rocky Hill, NJ). which is a known inducer of EMT that lead to the migration-(Lamouille and Derynck (2009)), with DMSO or with SD29-14 and the cells were allowed to grow for 20 h on Matrigel. After incubation, media and matrigels were carefully removed and adherent cells were washed three times with 1×PBS; to visualize cells, cells were incubated with Giemsa Stain (Sigma-Aldrich) (1:20 with water) for 10 minutes, washed in water until no blue color rinsed out from the well images under a Zeiss Compound microscope.

The results clearly show that without the drug treatment, the TGF on Matrigel induced the cells to develop extensive filipodia and lamellipodia for migration; whereas the drug-treated cells (treated with SD 29-14) cells show an inhibition of the filipodia and lamellipodia development. This result supports RACK1 protein involvement in the migration of selected cancer cells.

Figure 3:
FIG. 3 shows in side-by-side photomicrographs that a representative compound (SD 29-14) blocks filipodia development needed (for gaining potential to migrate) in another cell line MCF-7 (breast cancer) cells.

FIG. 3 shows in side-by-side photomicrographs that a representative compound (SD 29-14) blocks filipodia development needed (for gaining potential to migrate) in another cell lines MCF-7 (Breast cancer) cells. About 1×10^5 Breast cancer cells (MCF-7) treated with DMSO or SD29-14 for 48 h were resuspended in serum free MEM media and were then plated on 1:6 diluted (with serum free media) matrigel (Basement membrane mimic) in the presence of Transforming Growth Factor (TGFbeta) which is a known inducer of EMT that lead to the migration-(Lamouille and Derynck (2009)), with DMSO or with SD29-14 and the cells were allowed to grow for 20 h on Matrigel. After incubation, media and matrigels were carefully removed and adherent cells were washed three times with 1×PBS; to visualize cells, cells were incubated with Giemsa Stain (Sigma-Aldrich) (1:20 with water) for 10 minutes, washed in water until no blue color rinsed out from the well images under a Zeiss Compound microscope.

The results clearly show that in the absence of SD 29-14 treatment with the migration inducing TGF-beta resulted in the development of both filipodia and lamellipodia (red arrows) whereas when treated with the representative compound the development of both filipodia and lamellipodia was inhibited which sometimes appears as abortive (arrows) in the presence of the SD 29-14. The implication is inhibiting RACK1 Y246 phosphorylation (equivalent to pY248 in plants) with a RACK1-inhibiting drug (a compound of formula (1), (2) and/or (3)) on both breast and brain cancer cells indicate that the compounds may be used on diverse cancers where upregulation of RACK1 protein has been found to induce metastasis of cancers.

Figure 4:
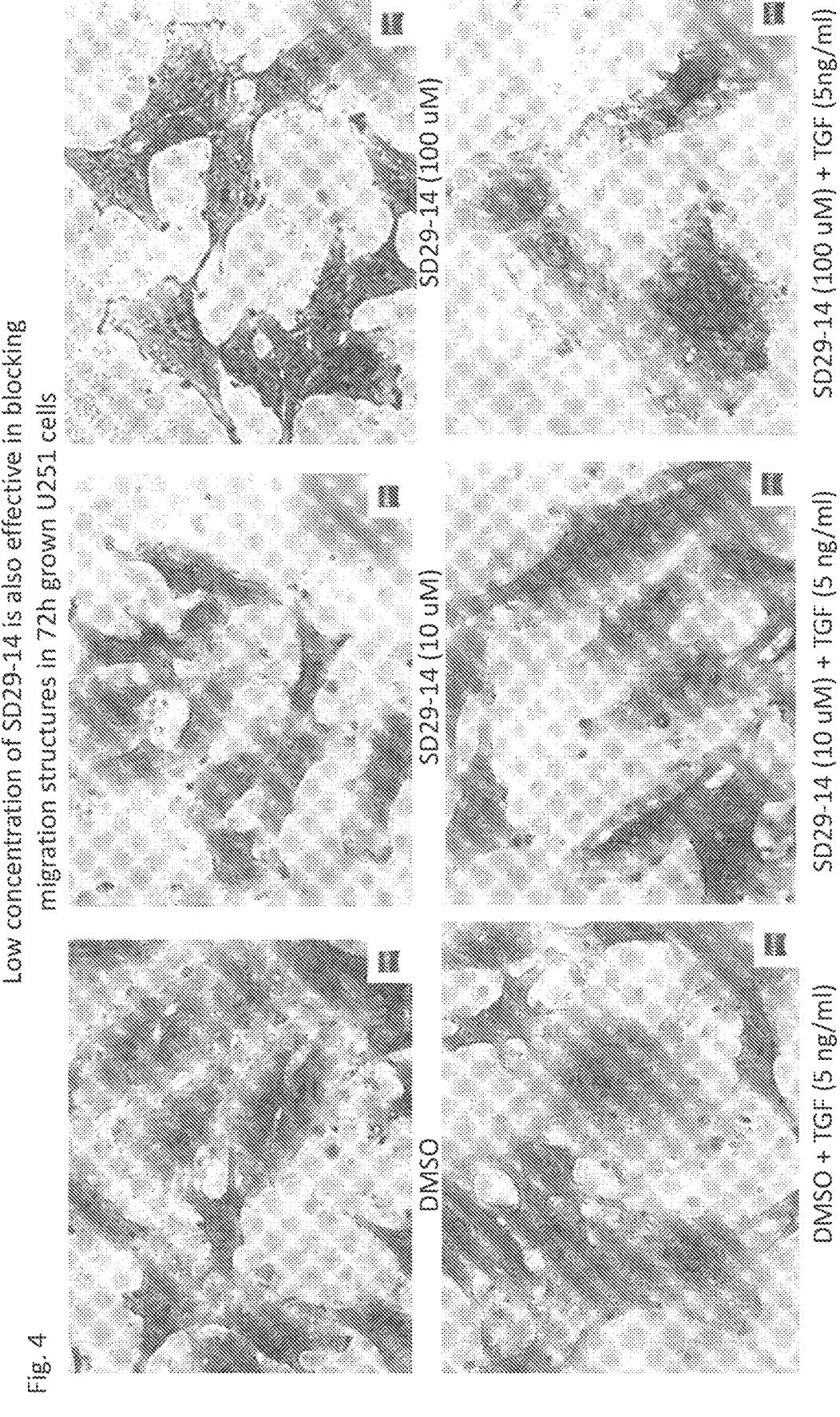
FIG. 4 shows in a series of six photomicrographs in a comparison against a control that a low concentration of a representative compound SD 29-14 is also effective in blocking migration structures in 72 h grown U251 cells.

FIG. 4 shows in a series of six photomicrographs in a comparison against a control that a low concentration of a representative compound SD 29-14 is also effective in blocking migration structures in 72 h grown U251 cells. It is shown in the FIG. 2 and FIG. 3 that 100 uM of SD 29-14 is effective in inhibiting the migration potential of the two different representative cancer cell lines, which establishes this drug as a candidate anti-metastasis drug for treating against cancers where a role of RACK1 upregulation is or has been shown in the metastasis process. There are many reviews on the RACK1 protein the cancer cell migration (e.g., Li and Xie, 2015; Duff and Long, 2017, among others).

However, 100 µM might be a high concentration or dosing and may be higher than physiologically potent concentration. As evident from the uniform DAPI treated cell nucleus in the drug treated vs non-treated cells in the immunofluorescence experiments, the cells were apparently not exposed to a toxic amount of the representative compound (SD 29-14).

Efficacy for inhibiting migration at a lower concentration of a representative compound was also investigated. Cancer cell lines were treated under conditions as used above for FIG. 2 and FIG. 3 but with both 10 µM and 100 µM SD29-14. As can be seen in the FIG. 4 (with U251 cells) and FIG. 5 (MCF-7 cells), the efficacy of a representative compound as the drug to inhibit filipodia and lamellipodia development is maintained with 10 µM (10-fold lower concentration from the experiments depicted in FIG. 2 and FIG. 3).

FIG. 5 shows in a series of photomicrographs in a comparison against a control that a low concentration of a representative compound (SD 29-14) is also effective in blocking migration structures in 72 h grown MCF-7 cells. The experimental methods, except for the different cell line, are essentially same as stated above as to FIG. 4.

Figure 6:
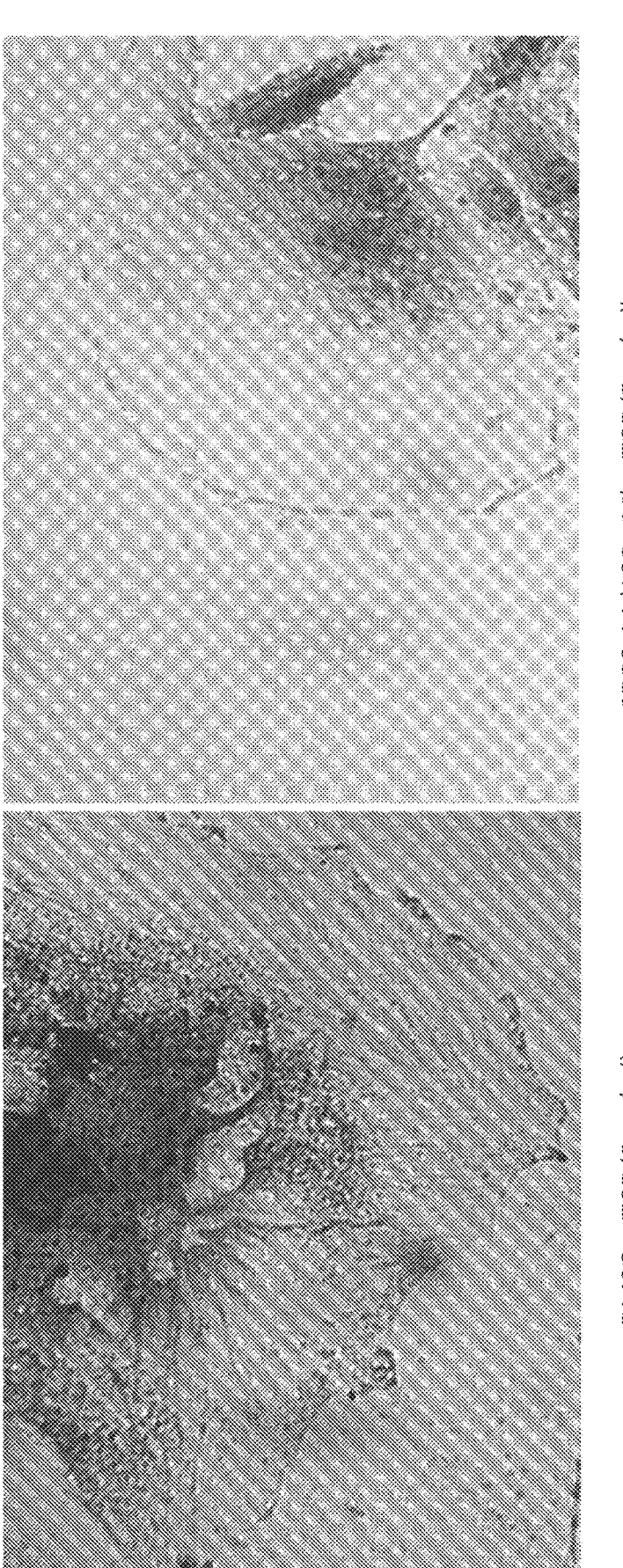
FIG. 6 shows in side-by-side photomicrographs a comparison between a control versus an exemplary dosing with a representative compound (SD 29-14) that the latter blocks actin stress fiber development in lamellipodia of U251 cells.

FIG. 6 shows in side-by-side photomicrographs a comparison between a control versus an exemplary dosing with a representative compound (SD 29-14) that the latter blocks actin stress fiber development in lamellipodia of U251 cells. Actin stress fibers are known to regulate the mesenchymal migrating cells by regulating the myosin-based contractility to achieve directional cell migration (Vallenius 2013). Radiating stress fibers within the developing lamellipodia are visible under a compound microscope in the DMSO treated U251 cells whereas the SD 29-14 treated cells, no visible stress fiber like radiating structures were visible. As these stress fibers are needed for other cellular functions required for directional movement, a lack of a visible stress fibers should inhibit cells treated with a representative compound (SD 29-14) from acquiring necessary traction generation to migrate. Actin stress fiber development has been reported to be needed to generate traction forces, establishment of the front-to-back polarity axis, retraction of the trailing edge, and extracellular matrix remodeling-development that collectively regulates the directional movement of migrating cell (Vallenius 2013). The cells were grown 72 h at conditions described for the cells imaged in FIG. 4 and were photographed under a Zeiss brand compound microscope at 40× magnification.

Figure 7:
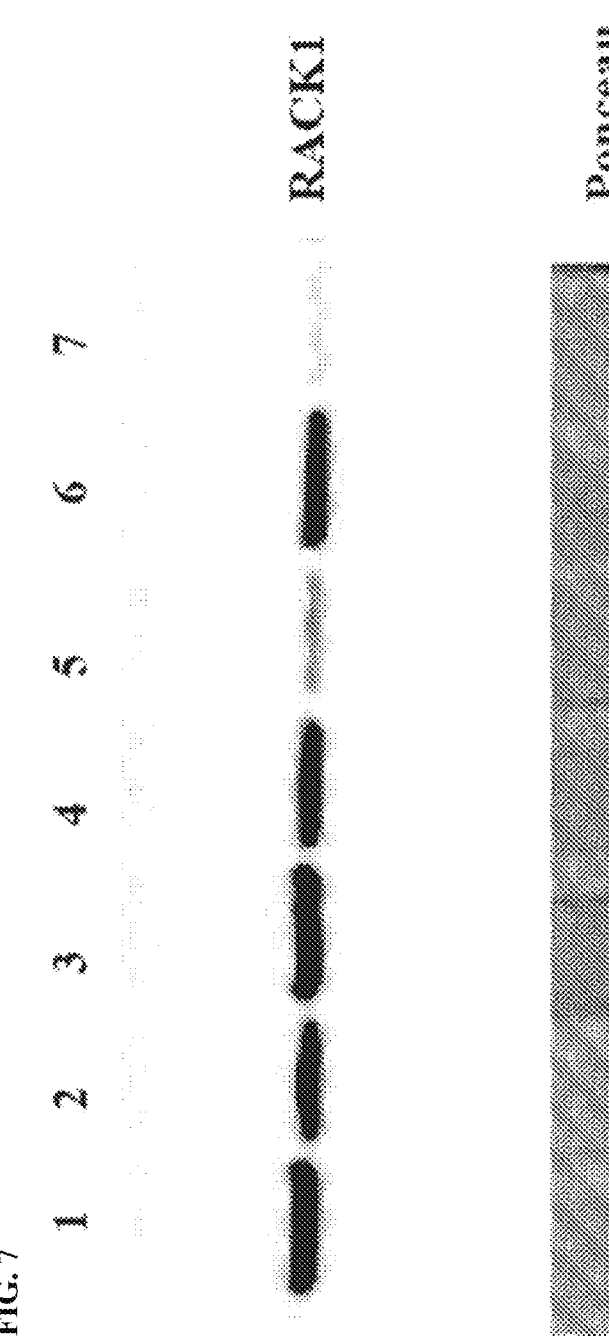
FIG. 7 shows RACK1 protein expression in MCF-7 cells treated with or without the representative compound (SD 29-14).

FIG. 7 shows RACK1 protein expression in MCF-7 cells treated with or without the representative compound (SD 29-14). The representative compound inhibits the tyrosine phosphorylation at the Y246 site in human RACK1 (corresponding to the *Arabidopsis* site Y248) protein and the lack of phosphorylation can potentially affect the RACK1 protein stability as can be seen in the figure. The SD 29-14 treated cells showed significant of RACK1 proteins (Lane 5 and 7).

As to FIG. 7, MCF-7 cells were washed three times in PBS after growth on MEM media for 6 days. The indicated compounds were added on day 1 and day 4 of the treatment. The cells were lysed in the lysis buffer (Cell Signaling, MA) supplemented with protease inhibitor cocktail (Sigma-Aldrich), Protein Tyrosine phosphatase inhibitors (Santa Cruz Biotechnology, TX), and N-Ethylamaleimide (Sigma-Aldrich) at 25 mM to inhibit de-sumoylation. Twenty five micrograms of proteins were loaded on the BIORAD company's 4-12% precast polyacrylamide gel, transferred to a PVDF membrane and then blocked with 5% non-fat milk (Biorad) for one hour, washed and incubated overnight at 4 C with the RACK1 antibody (1:2500 dilution) purchased from the Santa Cruz Biotechnology. After overnight incubation, the membrane was washed 3× in PBST and then incubated with a horseradish peroxidase-coupled mouse secondary antibody for an hour at room temperature and the bands were detected with enhanced chemiluminescence (Pierce, Rockford, IL, USA), according to standard methods. The lower panel shows the image of the same amount of proteins run on a BIORAD's TGX gels and transferred to a nitrocellulose membrane and stained with ponceau. This served as the loading control.

Figure 8:
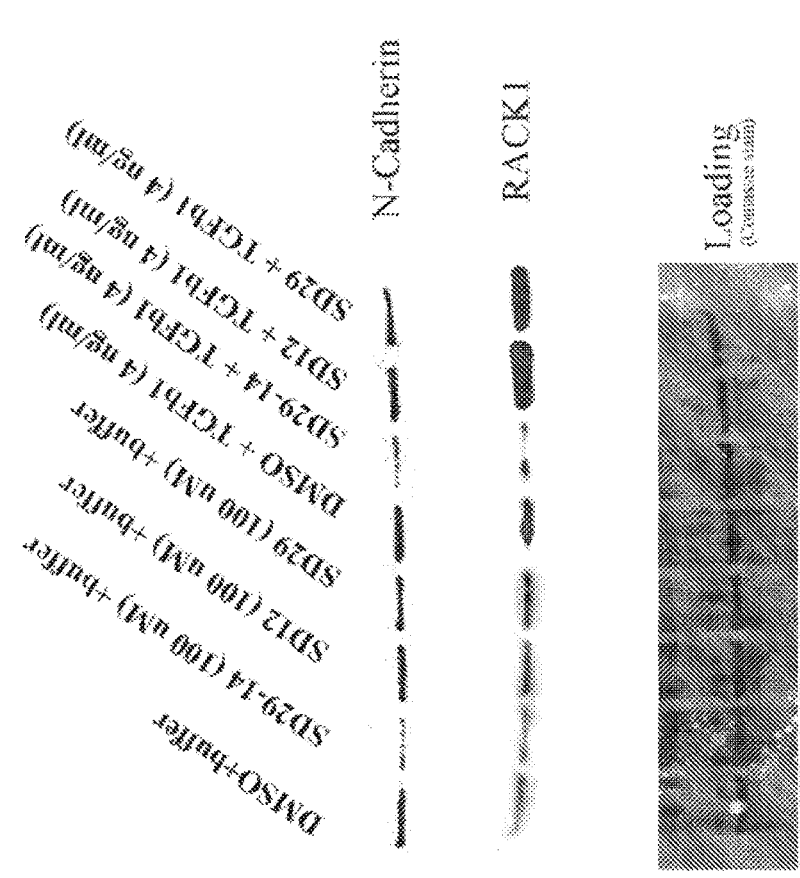
FIG. 8 shows protein expression of known EMT marker N-Cadherin in drug treated U251 cells. The inhibition of EMT marker by a representative compound (SD 29-14) in comparison to other compounds (SD 29, and SD 29-12).

FIG. 8 shows protein expression of known EMT marker N-cadherin in U251 cells treated with a representative compound as the drug. The inhibition of EMT marker by a representative compound (SD 29-14) in comparison to other compounds (SD 29, and SD 29-12). A large family of cadherin molecules are expressed in a cancer cell-type specific manner and among them, N-cadherin is reported to be expressed in mesenchymal cells (e.g., Li and Feng, 2011; Alizadeh et al., 2014). N-Cadherin expression has been found to be increased in diverse cancer metastasis, reported as one of the markers for mesenchymal cells, and is involved in adhesion of cells to stroma (Nieman et al., 1999; Hazan et al., 2000). Up-regulation of N-cadherin reduces cancer cell adhesion ability to epithelial cells, increases adhesion to stromal cells, and leads to subsequent invasion of tumor cells into stroma (Guan 2015). N-cadherin promotes cell migration and metastasis regardless of the expression and function of E-cadherin (Hazan et al., 2000). As can be seen in the FIG., the treatment of the representative compound SD 29-14 (not SD 29 and SD 29-12) as the drug is significantly apparently correlated with down-regulated N-cadherin expression indicating an inhibition of the EMT based motility of the cells from the treatment. The N-cadherin expression correlates with RACK1 expression (lower panel). The coomassie stained gel is used as the loading control.

As to FIG. 8, U251 cells starved (no serum) for 24 h and then treated with the indicated compounds with or without the TGFb and again replenished with the compounds and TGFb after 3 days. After allowing to grow for 6 days, the cells were washed three times in PBS. The cells were lysed in the lysis buffer (Cell Signaling, MA) supplemented with protease inhibitor cocktail (Sigma-Aldrich), Protein Tyrosine phosphatase inhibitors (Santa Cruz Biotechnology, TX), and N-Ethylamaleimide (Sigma-Aldrich) at 25 mM to inhibit de-sumoylation. Twenty five microgram of proteins were loaded on the BIORAD company's 4-12% precast polyacrylamide gel, transferred to a PVDF membrane and then blocked with 5% non-fat milk (Biorad) for one hour, washed and incubated overnight at 4 C with an N-cadherin antibody (Gene Tex, Irvine, CA) and a RACK1 antibody (after stripping) purchased from the Santa Cruz Biotechnology. After overnight incubation, the membrane was washed 3× in PBST and then incubated with a horseradish peroxidase-coupled secondary antibody for an hour at room temperature and the bands were detected with enhanced chemiluminescence (Pierce, Rockford, IL, USA), according to standard methods. The lower panel shows the coomassie gel image of the residual proteins left on the gel after transfer to the PVDF membrane.

Figure 9:
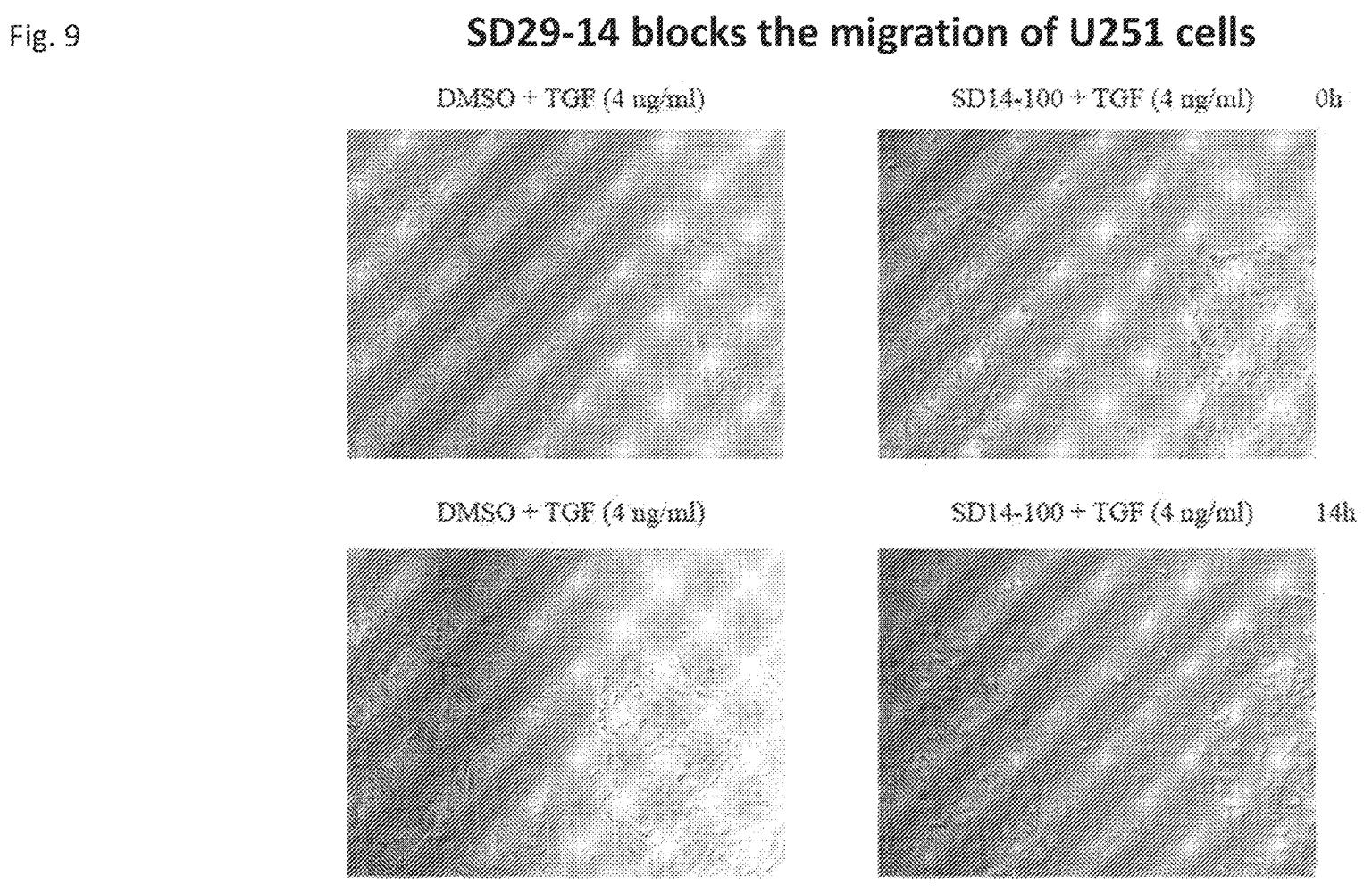
Figure 10:
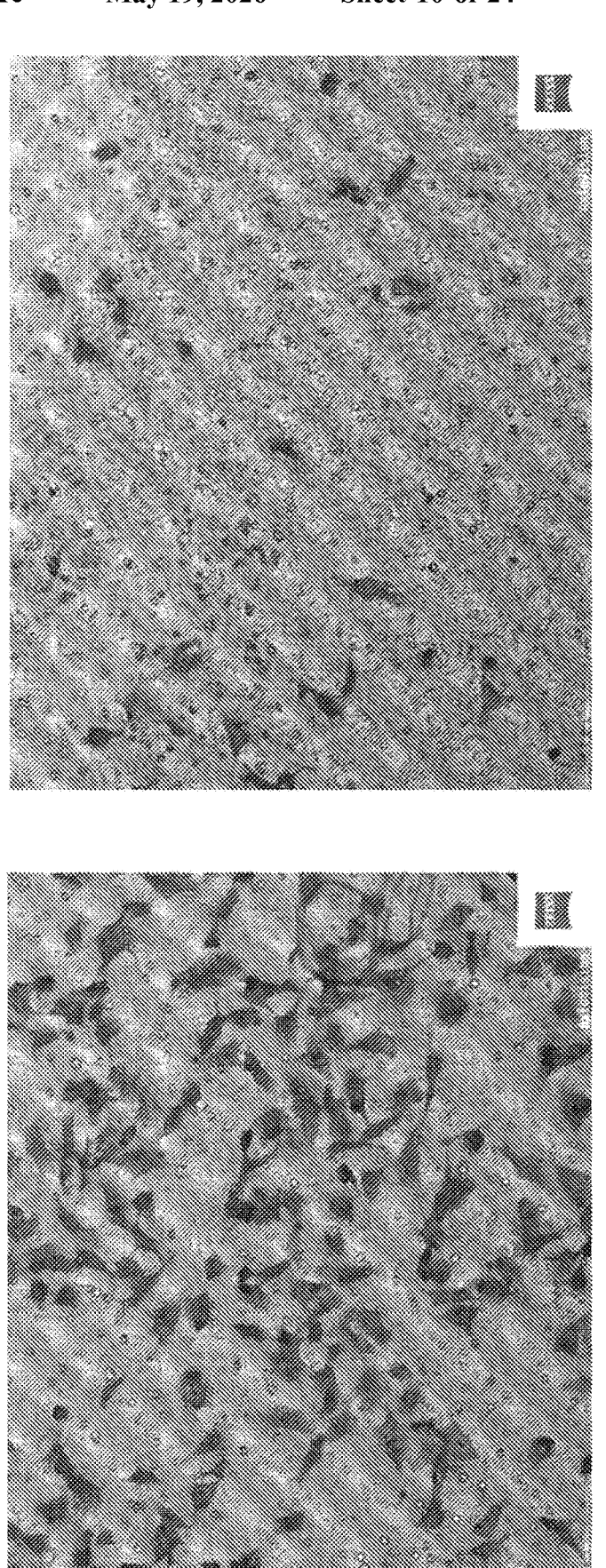

FIGS. 9 and 10 represents how SD 29-14 treatment to functionally inactivate RACK1 leads to the inhibition of migration (FIG. 9) and invasion (FIG. 10) of U251 cells.

During tumorigenesis, the epithelial-mesenchymal transition (EMT) plays a crucial role in migration and invasion of various cancers. EMT plays an essential role in tumor invasiveness and metastasis in cancer progression. Invasiveness (metastasis) of cancers is associated with a critical physiological process in which epithelial cells transition to mesenchymal transition or differentiation (EMT). Epithelial cells are not regarded as motile. However, in EMT, epithelial cells lose their epithelial characteristics, including their polarity (apical-basal polarity) and specialized cell-cell junctions, to acquire motility (migratory ability) behavior to become invasive mesenchymal cells, (e.g., Qu et al., Int. J. Clin. Exp. Med., 10 (6): 9019-9028 (2017); Xu et al., Cell Res. 19:156-172 (2009)). The motile mesenchymal cells can move (migrate) into surrounding tissue, even remote tissue. Therefore, assays were done to investigate the migration and invasion potential of U251 with or without treatment with a representative compound (SD 29-14). A wound was created by sliding a tip of a plastic pipette on the surface of almost 100 percent confluent cells and the size of the wound was measured at 0 h and after 14 h of wound creation. The migration of the cells to open areas in the wound reduces the size of the wound. Without the application of the representative compound (SD-29-14), the cells migrated to cover up the area of clearing but in the presence of the SD 29-14, the cells failed to migrate to cover the clear area created by the wound indicating that the cell migration potential was apparently suppressed (inhibited) the presence of SD 29-14.

In FIG. 10 and FIG. 11, U251 cells were plated in six-well plates and were allowed to reach about 90%-100% density. A wound was made using a 1 mL plastic pipette tip, then cells were washed with phosphate-buffered saline (PBS) two times and cultured in a medium containing 10% fetal bovine serum (FBS) at 37° C. The media was supplemented with 4 ng/ul TGF to induce migration. The size of wound was measured under a microscope at 0 and 14 h after wounding.

A transwell assay is conducted as a means for testing for invasion. A transwell invasion assay can be used to test the invasive potential of cells in response migration inducers or inhibitors. This assay is also known as modified Boyden chamber assay. During this assay, cells are placed on the upper layer of a cell culture insert with permeable membrane and a solution containing the test agent is placed below the cell permeable membrane. Following an incubation period (3-18 hours) at 37° C. in a humidified chamber, the cells that have stuck during the migration towards the lower chamber through the membrane are stained and counted. As can be seen when the U251 cells (0.5×10 ^5) are placed on the upper chamber with serum free media containing 2 ng/ul TGF and no SD 29-14 for about 14 hours, a large number cells were captured on the membrane when the cells tried to move towards the lower chamber with serum on the lower side of the membrane when the cells migratory action towards the media with serum which is visualized by crystal violet stain. There were hardly any cells were observed on the membrane when SD 29-14 was added to the cells on the upper chamber. Collectively, these findings (as shown in FIG. 9 and FIG. 10) indicate that administering a representative compound (SD 29-14) played a significant functional role in the regulation of U251 glioma cell migration and invasion.

In measuring cell invasion, 12-well transwell chambers (Corning Inc., Kennebunk, ME) were used with 6.5 mm inserts and 8.0 μm membrane pore size. U251 cells were plated on to the upper wells with 500 μL serum-free MEM media with or without SD29-14 (control cells treated with DMSO), and the bottom chamber filled with MEM containing 10% Fetal Bovine Serum (FBS). After the cells were incubated at 37° C. for 18 h, non-invasive cells on the top chambers were gently wiped with cotton wool. Invasive cells on the bottom surface were fixed with 4% paraformaldehyde for 15 min and stained with 0.2% crystal violet for 15 minutes and the cells were counted and photographed under a light microscope.

FIG. 11 presents side-by-side photomicrographs to compare a control versus representative dosing of U251 cells with a representative compound (SD 29-14) that shows the representative compound inhibits lamellipodia/filipodia co-localization of RACK1 with Extracellular Matrix (ECM) protein LamB1 in U251 cells. For effective migration, cell adhesion to the ECM is necessary and cell surface localized integrin molecules (alpha and beta) act as a link between the ECM and cell interior by acting as a receptor of the ECM proteins and linking ECM to the intracellular cytoskeleton complex. It is known that RACK1 acts as an integrin binding protein (Hermanto et al., 2002) and interaction between RACK1 and β1 integrin has been reported to mediate cancer cell invasion as reported in prostate cancer invasion and metastasis (Trerotola et al., 2012). RACK1 can promote tumor cell migration by using its scaffolding ability to bridge together different signaling proteins that integrate signaling from receptors cytoskeleton reorganization pathways. Laminin being a major ECM protein can therefor interact with integrins for cell adhesion and in this regard is expected to modulate by the RACK1 proteins scaffolding ability as discussed above. As can be seen in FIG. 11, treatment of U251 cells with TGFbeta1 to induce migration resulted in the co-localization of RACK1 (green) and Lamb1 (red) at the cell surface while this interaction was absent in the representative compound SD29-14 treated U251 cells (right panel). Lack of colocalization indicate that the link between the ECM proteins and intracellular cytoskeleton complex are interrupted and as such inhibiting this complex mediated migration signaling pathways.

As to FIG. 11, and methods of Immunofluorescence and confocal microscopy, U251 cells were grown to about 80% confluency in 12 well plate on glass cover slips and the cells were co-treated with the TGFb and indicated compounds for 72 h. After 72 h, the cells were fixed at room temperature with 4% paraformaldehyde-PBS for 15 minutes and then boiled for 10 minutes in 5% urea for antigen presentation. After 3× wash in PBST, the cells were permeabilized at room temperature by 0.5% Triton X-100-PBS (pH 7.4) for 10 min. The cells were then washed 3× with ice cold PBS. The cells were incubated with 3% BSA, 22.52 mg/mL glycine in PBST (PBS+0.1% Tween 20) for 30 min to block unspecific binding of the antibodies. The cells were incubated with 1:500 diluted anti-Lamb1 (Gene Tex, Irvine, CA) and 1:500 diluted anti-RACK1 antibody (Santa Cruz Biotechnology. Dallas, TX) in 1% BSA in PBST in a humidified chamber overnight at 4° C. The cells were washed three times in PBS, 5 min each wash and then incubated cells with the anti-rabbit TRITC (for Lamb1) and anti-rabbit FITC (for RACK1) conjugated secondary antibody in 1% BSA for 1 h at room temperature in the dark. After washing three times with PBST for 5 minutes each, the cells were mounted on slide using Prolong Slowfade Gold with DAPI (4=,6=-diamidino-2-phenylindole; Invitrogen), and confocal analysis was performed using Nikon CSU series Spinning Disk confocal microscope. Images were taken to show Laminin beta protein (red) and RACK1 protein (green) expression and localization. DAPI stained nuclear DNA was shown in blue. The bar represents 10 μm.

Figure 12:
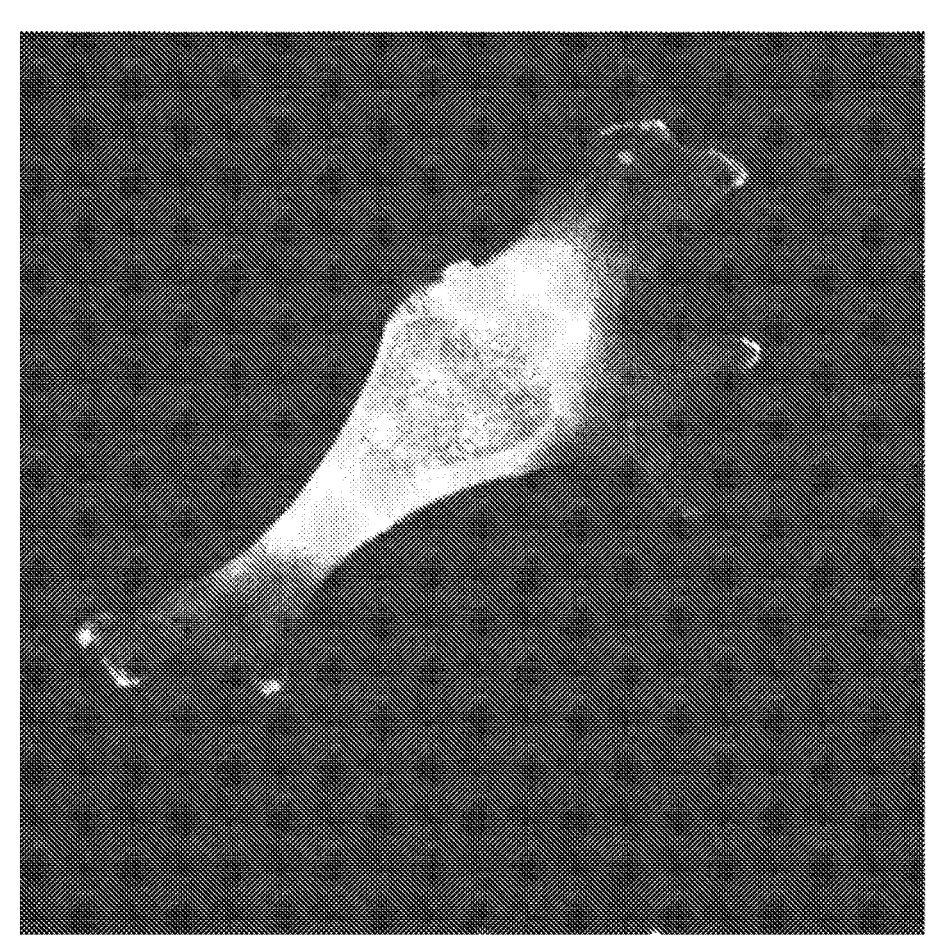
FIG. 12 is a photomicrograph that shows RACK1 and Focal Adhesion Kinase (FAK) co-localize in the tip of developing filipodia/lamellipodia on U251 cells.

FIG. 12 is a photomicrograph that shows RACK1 and focal adhesion kinase (FAK) co-localize in the tip of developing filipodia/lamellipodia on U251 cells. As discussed herein, integrin recruits FAK to establish supramolecular Focal adhesion complex. At FAK, RACK1 recruits key structural proteins, kinases and phosphatases to help nurture the developing focal adhesion. A change in RACK1 expression (both up and down) has consequences for the activity and stability of RACK1-associated proteins and is believed to be a contributing factor in the migration of the cancer cell. The FAK and RACK1 proteins are colocalized near the cell protrusion areas and an inability to co-localize will lead to the interruption in (inhibition of) the cell migration process. Adams, et al., Cell Communications and Signaling, 9:22 (2011).

Figure 13:
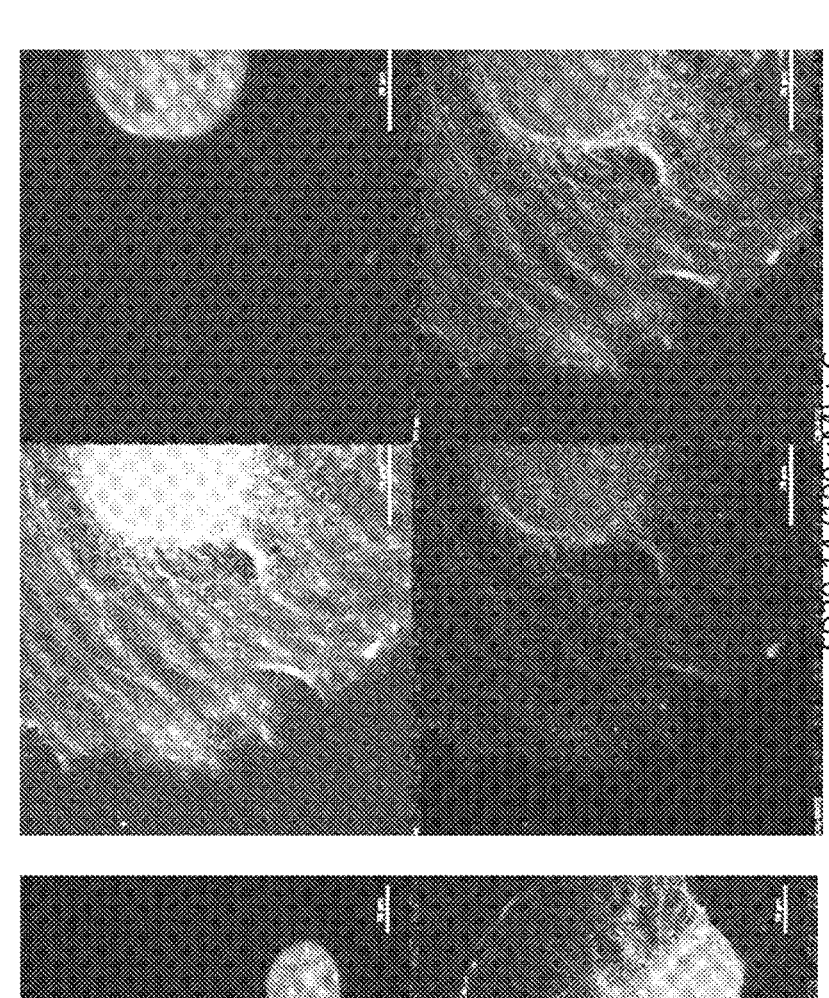
FIG. 13 presents in photomicrographs a comparison between an illustrative cancer in which the treatment involved using DMSO+TGF (5 ng/ml) as a control and the illustrative cancer cell in which the in vitro treatment involved using a compound according to a formulae (1), (2) and/or (3) herein+TGF (5 ng/ml).

FIG. 13 presents in photomicrographs a comparison between an illustrative cancer in which the treatment involved using DMSO+TGF (5 ng/ml) as a control and the illustrative cancer cell in which the in vitro treatment involved using a compound according to a formulae (1), (2) or (3) herein+TGF (5 ng/ml). The block of four photomicrographs on the left is for the control. The block of four photomicrographs on the right shows dosing with a representative compound (SD 29-14) blocks localization of FAK. Inability to co-localize would inhibit the downstream modifications of FAK reported as needed for migration.

As to FIGS. 12 and 13, cells were grown to almost 80% confluency and then serum starved for 24 hours. Then treated with the representative compound SD 29-14 for additional 24 h. No TGFbeta1 was used in this assay. After 24 h, cells were prepared for the immunofluorescence imaging essentially with the same procedure as described for FIG. 9. The antibody for the FAK was purchased from GeneTex (Irvine, CA). The secondary was rabbit TRITC. The primary RACK1 antibody coupled with a FITC reporter was purchased from Santa Cruz Biotechnology (Dallas, TX).

Figure 14:

FIG. 14 shows RACK1 tyrosine phosphorylation inhibitor compound SD 29-14 blocks Tyrosine397 phosphorylation of FAK in MCF-7 cancer cells.

RACK1 is reported to be an indispensable component in a so-called direction sensing pathway that includes the integrin effector FAK (focal adhesion kinase) and PDE4D5 (Li et al., Oncogene, 34 at 1895; Serrels et al., Curr. Biol. 20:1086-1092 (2010)). FAK has been reported as a signaling switch for diverse cellular functions, including cell motility and directional control as well as tissue invasion (e.g., Romer et al., Cir. Res., 98:606-616 (2006)). When the Tyr397 FAK tyrosine residue is auto-phosphorylated (also known as pY397-FAK), the development of a complex formation to assemble a focal adhesion structure or assembly has been described (e.g., Duff et al., Cellular Signaling, 35:250-255 (2017)). The complex or assembly has been associated with lamellipodia formation characteristic of cancer cell migration and invasion (metastasis). It has been reported that phosphorylated FAK is associated with enhanced motility (migration potential) of several cancer types and that phosphorylation of FAK can be increased by RACK1 but when RACK1 expression is suppressed, FAK is not phosphorylated on Tyr-397 and is not responsive to stimulation by the IGF-I receptor in cells (e.g., Kiely et al., J. Biol. Chem., 284 (30): 20263-20274 (2009)). Kiely et al. (2009) showed that association with RACK1 is required for FAK phosphorylation at Y397 and for the dephosphorylation at Y397 said to be tied to phosphorylation at RACK1 Y52.

It has been reported that inhibiting or disrupting, if not completely blocking, FAK phosphorylation and improper FAK localization can in turn inhibit or disrupt, if not block, development of lamellipodia and the cellular polarity that are associated with motility and invasiveness characteristic of cancer metastasis.

As to FIGS. 14 and 15, in order to evaluate the effect of a representative compound (SD 29-14) as a drug for inducing functional inactivation of RACK1 on the FAK phosphorylation, the drug was used in testing with breast cancer cells (MCF7, FIG. 14) and with glioblastoma cancer cells (U251, FIG. 15). In this immunofluorescence experiment, the pY397-FAK expressing cells were stained with FITC tagged secondary antibody (green) and RACK1 was stained with TRITC tagged secondary antibody (red). Here 5 ng/ml TGFbeta was used to induce cell migration. As can be seen in the left panel of the FIGS. 14 and 15, without the administration of the representative compound (SD 29-14), the expression of the pY397-FAK at the cell protrusions are clearly visible as green outgrowth whereas these expressions are almost completely inhibited in the cancer cells to which SD29-14 was administrated. As discussed above, without the pY397-FAK present, the connection between the ECM and cell interiors will be disrupted which will inhibit the cell's potential to migrate by initiating the cell's adhesion to the ECM.

As to FIGS. 14 and 15, and the methods, the immunofluorescence experiments are essentially same as described with reference to FIG. 9 with a slight modification in the duration of the drug treatment. The cancer cells (MCF7 or U251) were incubated with a drug (SD 29-14) or with DMSO (left panel) for 96 h in the presence of 5 ng/ml TGF-beta. After indicated incubation period, the cells were fixed and stained with antibody as described for FIG. 9 methods.

22

Figure 16:
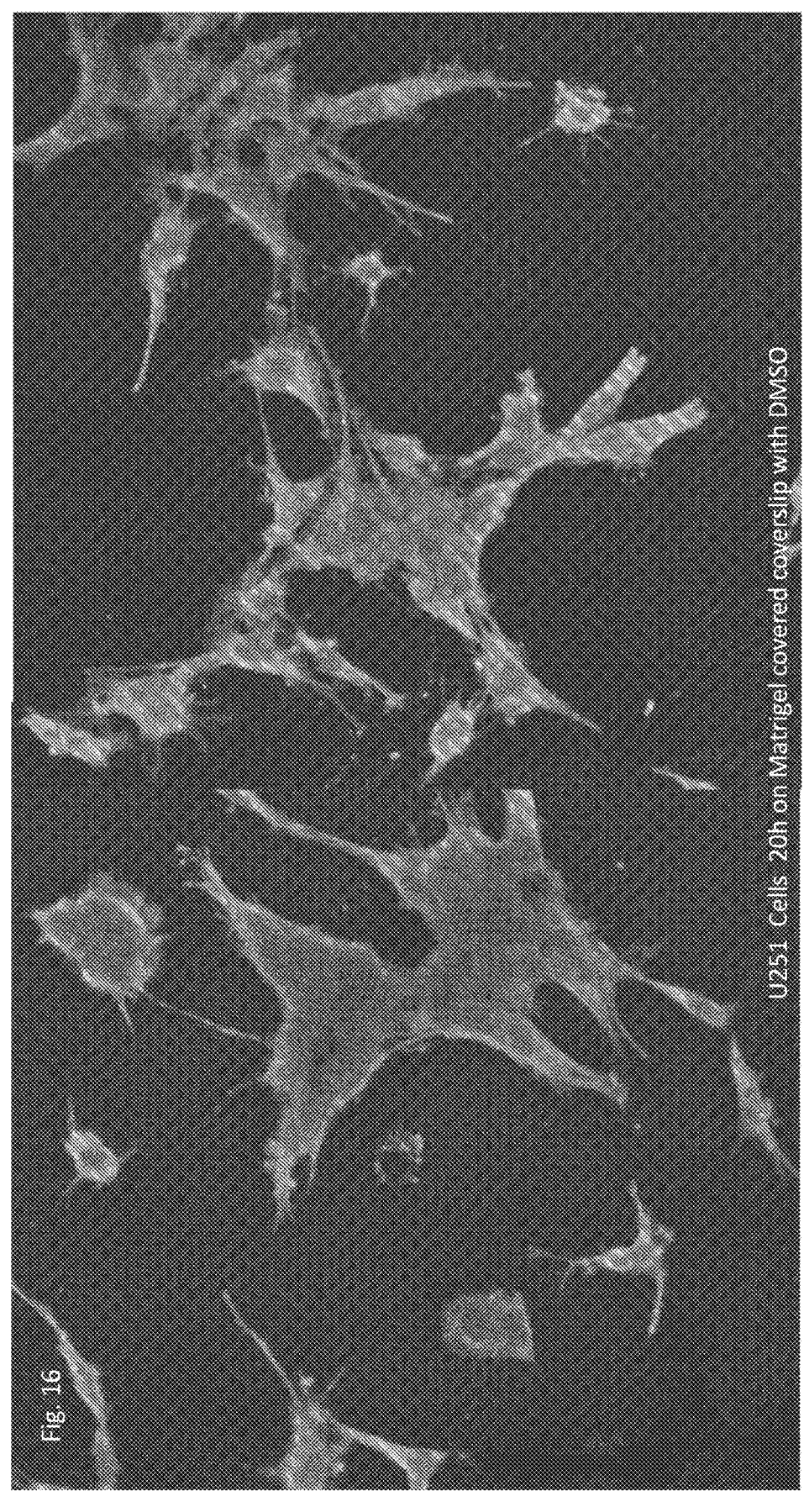
FIG. 16, 17, 18, 19 show a compound of formulas (1), (2) and (3), e.g. a SD 29-14 compound, inhibits cell shape differentiation during migration through Matrigel (as a basement membrane mimic).

FIG. 16, 17, 18, 19 show a representative compound (SD 29-14) inhibits cell shape differentiation during migration through Matrigel (a basement membrane mimic).

During cancer metastasis, the cells acquire cell-invasive behavior that accompanies their ability to adhere and migrate through the ECM. In order to migrate, the cells have to breach several basement membrane barriers. Basement membranes are a thin layer of connective tissues and functions as a supportive structure that forms a barrier between the epithelial and the underlying tissues. As a basement membrane mimic, matrigel is composed of laminin, collagen IV, heparan, various growth factors and is used to study the migration of cancer cells through the basement membrane.

FIG. 16 shows the migration of U251 cells through matrigel without any SD29-14 present. Within 24 h of the placement of the cells on the matrigel, the cells were able to migrate through the matrigel and were captured on the glass coverslip beneath the matrigel layer.

The cells developed long filipodia, invadopodia, and lamellipodia structures during the invasion whereas those structures where inhibited and the cells mostly maintained their cell-cell adhesion in the presence of 10 µM (FIG. 17) or in the presence of 100 µM (FIG. 18) of a representative compound (SD 29-14).

Figure 17:
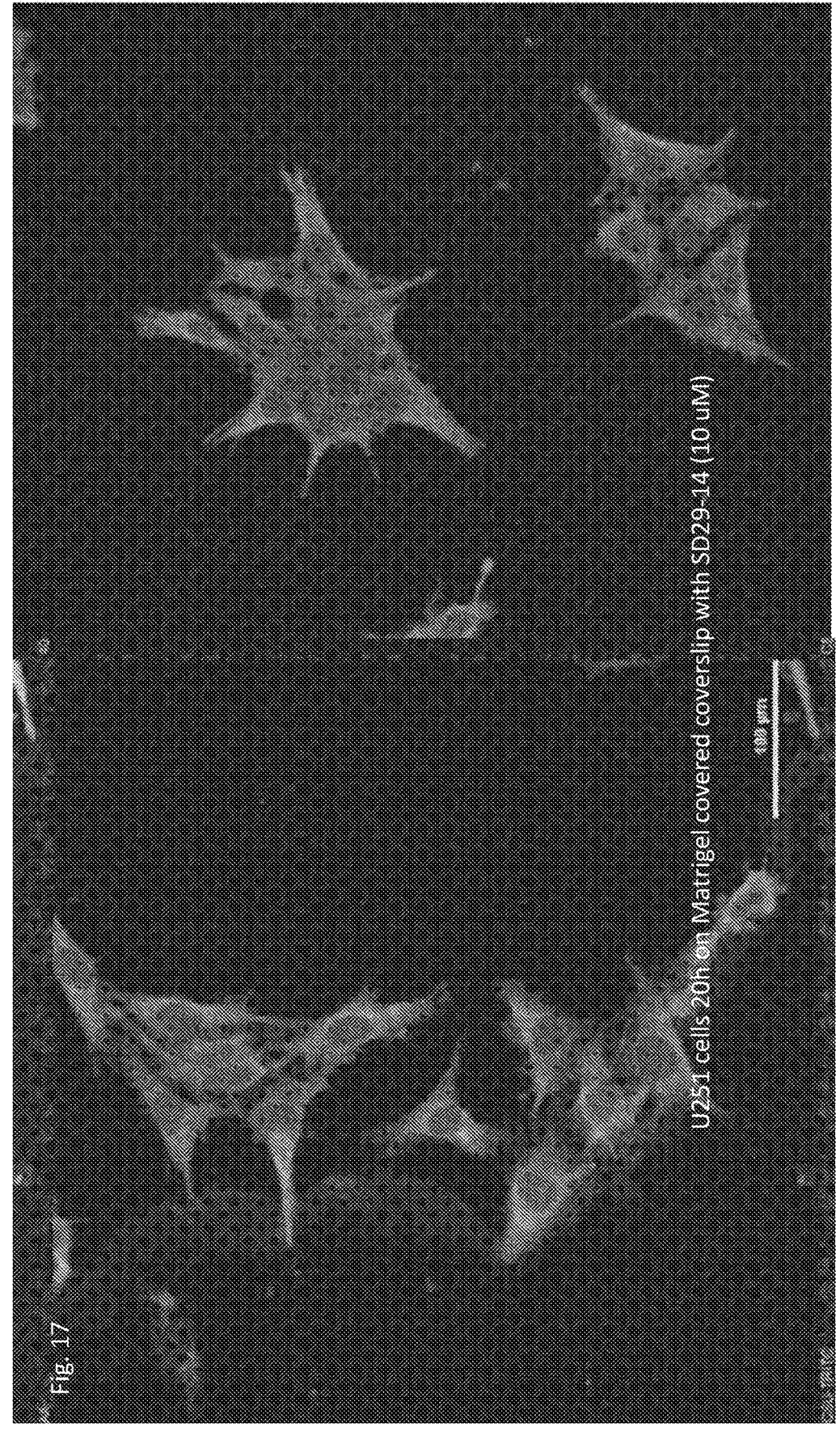
FIG. 17 in the presence of 10 uM of a representative compound (SD 29-14) filipodia, invadopodia, lamellipodia structures were inhibited and the U251 cells mostly maintained their cell-cell adhesion.
Figure 18:
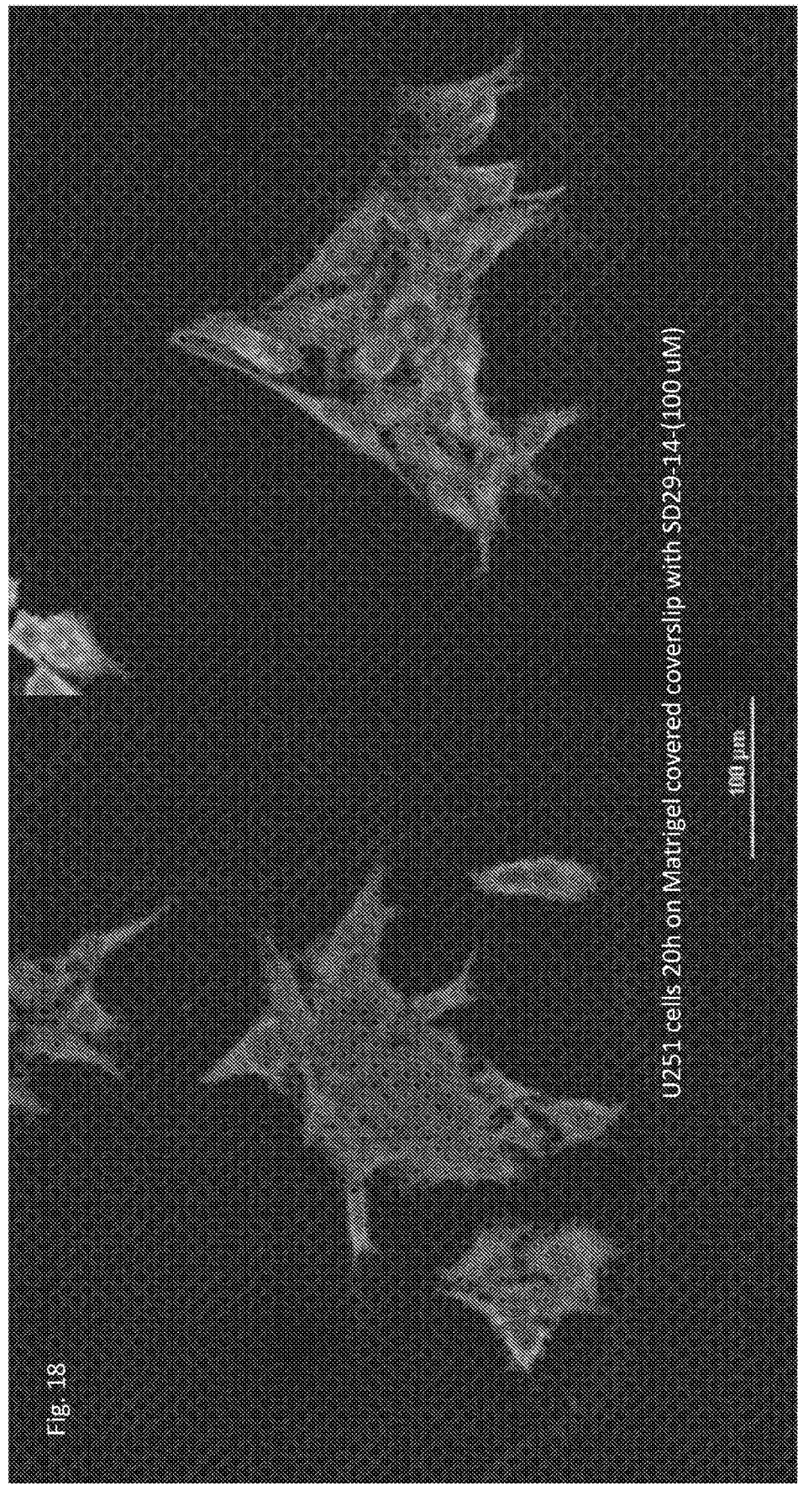
FIG. 18 in the presence of 100 uM of a representative compound (SD-29-14) filipodia, invadopodia, lamellipodia structures were inhibited and the U251 cells mostly maintained their cell-cell adhesion.
Figure 19:
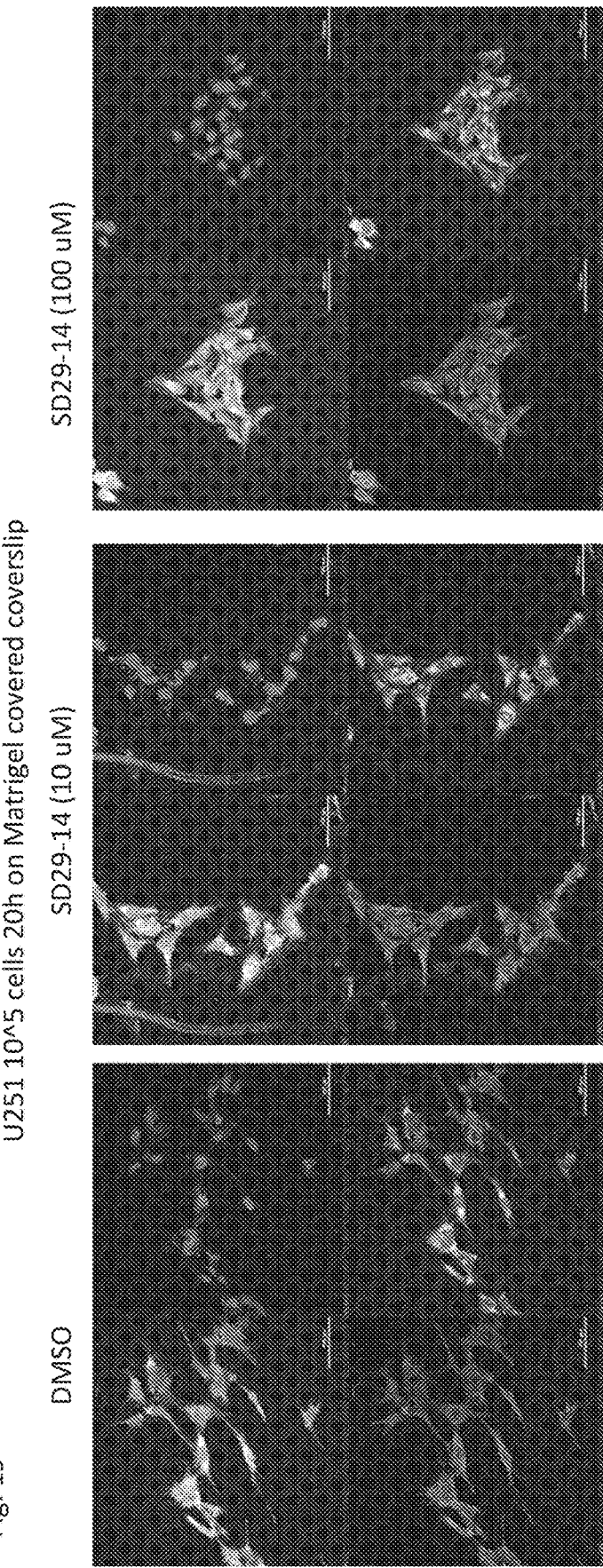
FIG. 19 shows the results of all three FIGS. 17, 17 and 18 in a panel.

FIG. 19 shows the results of all three FIGS. 16, 17 and 18 in a panel. The cells are labeled with an antibody (pY397-FAK) and detected with a rabbit-TRITC secondary antibody. The antibody staining allowed to visualize the cells clearly but the autofluorescence of the Matrigel made it hard to pinpoint the precise localization of the pY397-FAK protein. However, the results of the experiments are none-the-less significant and show it is possible to reduce the invasion potential of cancer cells by inhibiting RACK1 function with a representative compound (SD 29-14 compound), as can be seen in the migration through matrigel.

As to FIG. 19, and related methods, freshly harvested 10^5 cells in MEM no serum media+/−drugs (500 µl) placed on coverslip covered with 200 µl of 1:12 matrigel diluted with MEM serum free media in a 24 well plate. After 24 h, the matrigel was carefully removed by tilting wells and drawing from the tilted side of the wells and washing thoroughly with PBS to remove the matrigel completely (all crumbs removed as their auto fluorescence makes background during imaging) and then were fixed 10 minutes with 4% paraformaldehyde. Washed 2× with PBS; use 5% Urea to treat the cells at 95 C for 10 minutes, wash 2×PBS; permeabilize with 0.5% saponin in PBS; block cells with 3% BSA in PBST for 30 min; Overnight Primary antibody (ThermoFisher Cat #70025-pFAK397 rabbit at 1:250) in 1% BSA in PBST at 4 C, secondary (Rabbit-TRITC) also 1% BSA in PBST for one hour (1:1000).

FIG. 20 shows localized F-actin foci helps develop stress fiber based directional filopodia development while administration of a representative compound (SD 29-14) prevents organized filopodia development.

Cell cytoskeleton plays a significant role during the migration and invasion of cancer cells. Changes in the cytoskeleton accompanies the cell shape changes and which subsequently changes the dynamic actin polymerization and depolymerization process. The attachment of cells to the substrate is integrin dependent and as such it was postulated that the RACK1 dependent migration will also regulate the cytoskeleton changes. In this regard, F-actin foci helps stress fiber based directional filipodia development. To visualize F-actin, we used antibody anti-phalloidin that labels the F-actins. FAK located at focal contact which is actin based anchoring junction that links the cells with the ECM and mostly used by motile cells like the metastatic cancer cells. FAK is known as the key regulator of the F-actin dynamics (Li et al., 2013). (Li S Y, et al., Focal adhesion kinase is a regulator of F-actin dynamics: New insights from studies in the testis, *Spermatogenesis*, 3 (3): e25385 (2013).

In the absence of a representative compound (SD 29-14), the U251 cells can develop numerous F-actin foci in a non-symmetrical way (accumulating more towards the direction of migration) whereas treatment with a representative compound (SD 29-14) reduced the number and intensity of the F-actin foci, which is consistent with it reducing the migration capability of cancer cells. The presence of pY397-FAK can be seen in a linear organized way within the migratory structures but such organized presence of the pY397-FAK was not seen in the presence of the representative compound (SD29-14).

As to FIG. 20, and methods, U251 cells were grown on glass coverslip for 96 h in the presence or absence of SD29-14 containing MEM media with 2 ng/ml TGF-beta1 growth factor. After the incubation period, the immunofluorescence protocol as described in FIG. 9 was followed to label the F-actin and pY397-FAK antibodies.

FIG. 21 shows inhibition of vimentin (EMT marker) can prevent invasiveness of cancer cells.

FIG. 22 shows the effects at 10 μM concentration whereas FIG. 21 shows the effect at 100 μM concentration.

FIG. 23 illustrates a docking mode that shows SD29-14 as interacting with the OH group of Y246 of human RACK1—effectively inhibiting Y246 phosphorylation by blocking the OH group.

FIG. 24 illustrates a proposed model that draws from published literature that depicts the role of RACK1 (human) protein in the scaffolding complexes with key regulator proteins for migration through the development of lamellipodia/filopodia/invadopodium. RACK1 acts as versatile signaling hub for proteins regulating efficient invasion (migration and metastasis) of cancer cells, and that inhibiting active site(s) on RACK1, such as site Y246 not being phosphorylated, can impair migration of cancer cells.

As to the model illustrated in FIG. 24, RACK1 mediates cell spreading by establishing contact with the extracellular matrix (ECM) and ECM protein receptors-integrins at the focal adhesion sites. Integrin clustering is sufficient to promote the phosphorylation of FAK (Focal Adhesion Kinase) on Tyr-397. This in turn generates a binding site for the Src homology 2 (SH2) domain of Src Family protein tyrosine kinases (Src-family PTKs). The recruitment of Src-family PTKs to FAK is dependent on the initial autophosphorylation of Tyr-397. Phosphorylation of RACK1 on Tyr-246 is required for the binding to the Src. RACK1 is also reported as the substrate of Src for this phosphorylation. Binding of RACK1 to Src is essential to regulate FAK's function. Formation of RACK1$^{Y1246}$-Src-FAK$^{397}$ complex allows targeted phosphorylation of substrates at the focal adhesions and invadopodia by Src causing efficient invasion. Abolition of RACK1 Y246 phosphorylation breaks the complex and Src is free to phosphorylate substrate indiscriminately leading to migration impairment. Over-expression of N-cadherin is a marker of EMT (Epithelial to Mesenchymal Transition), which transition is a hallmark of cancer migration. In cells in culture, it is well known that the phosphotyrosine-proteins are highly accumulated at focal adhesions, reflecting the highly specific area of signal transduction. The stress fibers (actin-based) also apparently have a major role for migration. The formation of lamellipodia been attributed to a combined role of F-actin and associated proteins and EMT marker intermediate filament vimentin. Vimentin plays an integral role in the lamellipodia formation and polarity maintenance in migrating cells. Vimentin though localized at leading edge of the membrane of invading cells, disassembly of the vimentin from the leading edge within the lamellipodia towards the cell interior has been shown to be necessary for formation of cellular polarity, leading to an increase in migration. When vimentin filaments were disrupted using a dominant-negative vimentin probe, there was a significant decrease in formation of mature invadopodia (Schoumacher et al., 2010). For simplicity only few actin and vimentin complexes in the lamellipodia formation are depicted in the model. Adams et al. (2011).

The complete disclosures of all patents and literature referenced herein are incorporated herein by reference. References include:

Adams et al., RACK1, A multifaceted scaffolding protein: Structure and function, Cell Communication and Signaling, 9:22 (2011)

A M Alizadeh, S. Shiri, S. Farsinejad, Metastasis review: from bench to bedside, Tumour Biol., 35:8483-8523 (2014)

Bowen Du and Joong Sup Shim (2016) Targeting Epithelial-Mesenchymal Transition (EMT) to Overcome Drug Resistance in Cancer Molecules 2016, 21, 965; doi: 10.3390/molecules21070965

Chang et al, J Biol. Chem., 276:20346-20356 (2001)

Chen et al., Cancer Res., 75 (18): 3832-3841 (2015)

Choi et al., Oncotarget, 6 (6): 4451-4466 (2015)

Dave et al., J. Biol. Chem. 288 (42): 30720-30733 (2013)

Du and Shim, Targeting Epithelial-Mesenchymal Transition (TMT) to Overcome Drug Resistance in Cancer, Molecules, 21:965 (2016)

Duff et al., Cellular Signalling, 35:250-255 (2017)

Einhorn et al., Ecole Normal Supérieure de Lyon, BioSciences Master Reviews, November 2013, pp. 1-9

Guan, X. (2015) Cancer metastases: challenges and opportunities. Acta Pharmaceutica Sinica B. V 5 Issue 5 (September 2015). Pp 402-418.

Jianjun Guo, Junbi Wang; Li Xi, Wei-Dong Huang, Jiansheng Liang and Jin-Gui Chen1, (2009) RACK1 is a negative regulator of ABA responses in *Arabidopsis*. Journal of Experimental Botany, Vol. 60, No. 13, pp. 3819-3833

Havel et al., Oncogene, 34 (15): 1979-1990 (Apr. 9, 2015)

R B Hazan, G R Phillips, R F Qiao, L. Norton, S A. Aaronson, Exogenous expression of N-cadherin in breast cancer cells induces cell migration, invasion, and metastasis, J. Cell Biol., 148:779-790 (2000)

Hermanto U, Zong C S, Li W, Wang L H: RACK1, an insulin-like growth factor I (IGF-I) receptor-interacting protein, modulates IGF-I-dependent integrin signaling and promotes cell spreading and contact with extracellular matrix, Mol Cell Biol. 2002, 22:2345-2365. 10.1128/MCB.22.7.2345-2365.2002

Kidd et al., Transactional Rev., Am. J. Resp. Cell. Mol. Biol., 50 (1): 1-6 (2014)

Kiely P A, Baillie G S, Barrett R, Buckley D A, Adams D R, Houslay M D, O'Connor R: Phosphorylation of RACK1 on tyrosine 52 by c-Abl is required for insulin-like growth factor I-mediated regulation of focal adhesion kinase, J Biol Chem., 284:20263-20274 (2009).

Kiely M, Adams D R, Hayes S L, O'Connor R, Baillie G S, Kiely P A. (2016) RACK1 stabilises the activity of PP2A to regulate the transformed phenotype in mammary epithelial cells, Cell Signal. 35:290-300 (July 2017); doi: 10.1016/j.cellsig.2016.09.001. Epub 2016 Sep. 4.

Kundu N, Dozier U, Deslandes L, Somssich I E, Ullah H. (2013) *Arabidopsis* scaffold protein RACK1A interacts with diverse environmental stress and photosynthesis related proteins, *Plant Signal Behav.* 2013; 8 (5): e24012.

Lahat et al., PLosOne, 5 (4): 1-19 (2010)

Lamouille et al., Nat. Rev. Mol. Cell Biol., 15 (3): 178-196 (March 2014)

Li et al., Oncogene, 34:1890-1898 (2015)

D M Li, Y M Feng, Signalling mechanism of cell adhesion molecules in breast cancer metastasis: potential therapeutic targets, Breast Cancer Res. Treat., 128:7-21 (2011)

Liliental J, et al., Rack1, receptor for activated protein kinase C, interacts with integrin beta subunit, J Biol Chem. 1998, 273:2379-2383. 10.1074/jbc.273.4.2379.

Lin et al., Int'l J. Oncology, 44 (4): 1252-1258 (2014)

Lu et al., Oncol. Rep. 27:1646-1652 (2012)

Lv Q L et al., Overexpression of RACK1 Promotes Metastasis by Enhancing Epithelial-Mesenchymal Transition and Predicts Poor Prognosis in Human Glioma, *Int J Environ Res Public Health.*, 13 (10): 1021 (Oct. 18, 2016)

McInroy et al., Biochem. Biophys. Res. Comm., 360 (1): 109-114 (2007)).

Mamidipudi V, Chang B Y, Harte R A, Lee K C, Cartwright C A: RACK1 inhibits the serum- and anchorage-independent growth of v-Src transformed cells, FEBS Lett. 2004, 567:321-326. 10.1016/j.febslet.2004.03.125.

Mamidipudi V, Zhang J, Lee K C, Cartwright C A: RACK1 regulates G1/S progression by suppressing Src kinase activity, Mol Cell Biol. 2004, 24:6788-6798. 10.1128/MCB.24.15.6788-6798.2004.

M T Niemann. R S Prudoff, K R Johnson, M J Wheelock, N-cadherin promotes motility in human breast cancer cells regardless of their E-cadherin expression, J. Cell Biol., 147:631-644 (1999)

Onishi I, et al., RACK1 associates with NHE5 in focal adhesions and positively regulates the transporter activity, Cell Signal. 2007, 19:194-203. 10.1016/j.cellsig.2006.06.011

Peng et al., Oncol. Rep. 30:2195-2202 (2013)

Geping Q U, Changting Liu, Xiangqun Fang, Zhijian Zhang, Baojun Sun, Peng Wang, RACK1 as a potential prognostic biomarker and regulator of epithelial-mesenchymal transition in non-small cell lung cancer, Int. J. Clin. Exp. Med., 10 (6): 9019-9028 (2017)).

Quadri, Microvasc Res., 83 (1): 3-11 (January 2012)

Romer L H, Birukov K G, Garcia J G: Focal adhesions: paradigm for a signaling nexus, Circ Res., 98:606-616 (2006). 10.1161/01.RES.0000207408.31270.db.

Ruan et al., J. Clin. Invest., 122 (7): 2554-2566 (2012)

Sabila, M.; Kundu, N.; Smalls, D.; and Ullah, H. (2016), Tyrosine Phosphorylation Based Homo-dimerization of *Arabidopsis* RACK1A Proteins Regulates Oxidative Stress Signaling Pathways in Yeast, Front. Plant Sci., 24 Feb. 2016, https://doi.org/10.3389/fpls.2016.00176 Serrels et al., Curr. Biol. 20:1086-1092 (2010)

Shen et al., Molecular Medicine Reports, 8:999-1004 (2013)

Schoumacher et al., Actin, microtubules, and vimentin intermediate filaments cooperate for elongation of invadopodia, *J Cell Biol.,* 189:541-556 (2010).

Li S Y et al., Focal adhesion kinase is a regulator of F-actin dynamics: New insights from studies in the testis, *Spermatogenesis.* 2013; 3 (3): e25385.)

Trerotola et al., Trop-2 inhibits prostate cancer cell adhesion to fibronectin through the β1 integrin-RACK1 axis, J. Cell. Physiol., 227:3670-3677 (2012)

Ullah et al, Structure of a signal transduction regulator, RACK1, from *Arabidopsis thaliana*, Protein Science, 17:1771-1780 (2008)

Vallenius T., Actin stress fibre subtypes in mesenchymal-migrating cells. *Open Biol.,* 3 (6): 130001 (2013), doi: 10.1098/rsob.130001

Wang N, Liu F, Cao F, et al. RACK1 predicts poor prognosis and regulates progression of esophageal squamous cell carcinoma through its epithelial-mesenchymal transition, *Cancer Biol Ther.* 16 (4): 528-540 (April 2015)

Wang et al., Oncology Letters, 9:2767-2770 (2015)

Wang et al., Cellular Biochem., 438 (1-2): 47-57 (2018)

Xu J, Lamouille S, Derynck R. (2009) TGF-beta-induced epithelial to mesenchymal transition, Cell Res., 19 (2): 156-72 (February 2009)

The invention claimed is:

1. A method for treating a cancer comprising administering to a subject in need thereof a compound, a tautomer of the compound, or a pharmaceutically acceptable salt of the compound or of the tautomer in an amount effective for inhibiting metastasis of the cancer, wherein the compound is represented by the formula:

wherein each $R_1$ is independent of the other and represents a halogen atom selected from the group consisting bromine, chlorine, fluorine and iodine,
wherein the cancer is breast cancer or glioblastoma in which RACK1 functions as a positive regulator for cancer cell migration and metastasis.

2. The method according to claim 1, wherein each $R_1$ is the same.

3. The method according to claim 1, wherein at least one $R_1$ represents chlorine.

4. The method according to claim 2, wherein each $R_1$ represents chlorine.

5. A method for treating a cancer metastasis comprising administering to a subject in need thereof a compound, a tautomer of the compound, or a pharmaceutically acceptable salt of the compound or of the tautomer, wherein the compound is represented by the formula:

wherein each $R_1$ is independent of the other and represents a halogen atom selected from the group consisting of bromine, chlorine, fluorine and iodine,
wherein the cancer is breast cancer or glioblastoma in which RACK1 functions as a positive regulator for cancer cell migration and metastasis.

6. The method according to claim 5, wherein each $R_1$ is the same.

7. The method according to claim 5, wherein at least one $R_1$ represents chlorine.

8. The method according to claim 5, wherein each $R_1$ represents chlorine.

* * * * *